(12) United States Patent
Brown et al.

(10) Patent No.: US 10,989,810 B2
(45) Date of Patent: Apr. 27, 2021

(54) SYSTEMS AND METHODS FOR BEAMFORMING USING VARIABLE SAMPLING

(71) Applicant: DALHOUSIE UNIVERSITY, Halifax (CA)

(72) Inventors: Jeremy Brown, Halifax (CA); Christopher Samson, Samson's Cove (CA); Jeff Leadbetter, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 905 days.

(21) Appl. No.: 15/544,778

(22) PCT Filed: Jan. 22, 2016

(86) PCT No.: PCT/CA2016/050054
§ 371 (c)(1),
(2) Date: Jul. 19, 2017

(87) PCT Pub. No.: WO2016/115638
PCT Pub. Date: Jul. 28, 2016

(65) Prior Publication Data
US 2018/0011193 A1 Jan. 11, 2018

Related U.S. Application Data

(60) Provisional application No. 62/107,192, filed on Jan. 23, 2015, provisional application No. 62/158,409, filed on May 7, 2015.

(51) Int. Cl.
*A61B 8/00* (2006.01)
*G01S 15/89* (2006.01)
(Continued)

(52) U.S. Cl.
CPC ............ *G01S 15/8918* (2013.01); *A61B 8/12* (2013.01); *A61B 8/14* (2013.01); *A61B 8/4483* (2013.01);
(Continued)

(58) Field of Classification Search
CPC ........... A61B 8/12; A61B 8/14; A61B 8/4483; A61B 8/5207; G01S 15/8915;
(Continued)

(56) References Cited

U.S. PATENT DOCUMENTS 4,669,314 A 6/1987 Magrane
6,705,995 B1 3/2004 Poland et al.
(Continued)

FOREIGN PATENT DOCUMENTS

EP 2466330 A2 6/2012
EP 2741103 11/2014
WO 2014125371 A1 8/2014

OTHER PUBLICATIONS

Bezanson et al., "Fabrication and performance of a miniaturized 64-element high-frequency endoscopic phased array", IEEE Transactions on Ultrasonics, vol. 61, Issue 1, pp. 33-43, Published Jan. 6, 2014 (Year: 2014).*

(Continued)

*Primary Examiner* — Christopher L Cook
(74) *Attorney, Agent, or Firm* — Hill & Schumacher

(57) ABSTRACT

The present disclosure provides systems and methods for ultrasound imaging using a modified variable sampling beamforming technique. Unlike conventional methods of variable sampling beamforming, in which in-phase and quadrature samples are obtained for each pixel location, in various example embodiments of the present disclosure, the pixel locations are quadrature-spaced such that for each 5 sample point, an adjacent sample point along an A-line is (Continued)

employed as the quadrature sample. The samples at each array element may be triggered according to the time of flight between a first pixel location and the location of the array element, such that successive samples, corresponding to successive pixel locations along the selected A-line, are obtained such that adjacent samples are spaced by a 10 time interval corresponding to a quarter of an odd number of wavelenghths of the beamformed transmit pulse, and such that only one sample is acquired per pixel.

29 Claims, 17 Drawing Sheets

(51) Int. Cl.
  *A61B 8/14* (2006.01)
  *G01S 7/52* (2006.01)
  *A61B 8/12* (2006.01)
  *G10K 11/34* (2006.01)
  *A61B 8/08* (2006.01)

(52) U.S. Cl.
  CPC .......... *A61B 8/5207* (2013.01); *G01S 7/5208* (2013.01); *G01S 7/52028* (2013.01); *G01S 7/52034* (2013.01); *G01S 15/8915* (2013.01); *G10K 11/341* (2013.01)

(58) Field of Classification Search
  CPC ............. G01S 15/8918; G01S 7/52028; G01S 7/52034; G01S 7/5208
  See application file for complete search history.

(56) References Cited

U.S. PATENT DOCUMENTS

| | | |
|---|---|---|
| 7,819,805 B2 | 10/2010 | Davies et al. |
| 8,836,557 B2 | 9/2014 | Eldar et al. |
| 2007/0239001 A1* | 10/2007 | Mehi .................. G01S 15/8927 600/437 |
| 2013/0109969 A1 | 5/2013 | Kim et al. |
| 2014/0036091 A1 | 2/2014 | Zalev et al. |
| 2014/0066759 A1 | 3/2014 | Healey |
| 2014/0200455 A1 | 7/2014 | Rigby |

OTHER PUBLICATIONS

Wagner et al., "Compressed Beamforming in Ultrasound Imaging", IEEE Transactions on Signal Processing, vol. 60, Isssue 9 (Year: 2012).*

Yoshiki Yamakoshi, "Fetal heart Rate Estimation by an Ultrasonic Wave Direct Digital Detection and Complex Auto Correlation", The Journal of the Institute of Electronics, Information and Communication engineers, Japan, Dec. 2001, A vol. J84-A No. 12, 1414-1420, with Partial English translation.

Jorge Camacho, "Phase Coherence Imaging", IEEE Transcation on Ultrasonics, Ferroelectrics, and Frequency Control, the United States, May 2009, vol. 56, No. 5, 958-974.

International Search Report (PCT/CA016/050054) dated May 4, 2016.

Written Opinion (PCT/CA2016/050054) dated May 4, 2016.

Brown et al., "A digital beamformer for high-frequency annular arrays", IEEE Transactions on ultrasonics, ferroelectrics and frequency control, vol. 52, No. 8, p. 1262-1269, Aug. 2005.

Powers et al., "Ultrasound phased array delay lines based on quadrature sampling techniques", IEEE Transactions on sonics and ultrasonics, vol. SU-27, No. 6, p. 287-294, Nov. 1980.

F. S. Foster, J. D. Larson, R. J. Pittaro, P. D. Corl, A. P.Greenstein, and P. K. Lum, "A digital annular array prototype scanner for realtime ultrasound imaging," Ultrasound Med. Biol., vol. 15, No. 7, pp. 661-672, 1989.

* cited by examiner

SYSTEMS AND METHODS FOR BEAMFORMING USING VARIABLE SAMPLING

CROSS-REFERENCE TO RELATED APPLICATION

This application claims priority to U.S. Provisional Application No. 62/158,409, titled "SYSTEMS AND METHODS FOR BEAMFORMING USING VARIABLE SAMPLING" and filed on May 7, 2015, the entire contents of which is incorporated herein by reference, and to U.S. Provisional Application No. 62/107,192, titled "SYSTEMS AND METHODS FOR BEAMFORMING USING VARIABLE SAMPLING" and filed on Jan. 23, 2015, the entire contents of which is incorporated herein by reference.

BACKGROUND

The present disclosure relates to systems and methods of ultrasound imaging and image beamforming.

Conventional low-frequency, large penetration, ultrasound imaging systems are based on large arrays of miniature transmitter-receiver elements referred to as a transducer array. By using a transducer array, made of many individually addressed transduction elements, the effective curvature of the aperture can be changed electronically, resulting in a much better image quality. This is because the ultrasound energy can be focused and steered off to different angles. High-frequency ultrasound, on the other hand, is a relatively new technology that uses micro-fabricated imaging arrays that are capable of an order of magnitude higher resolution than conventional ultrasound systems currently used in diagnostic imaging. Although resolution increases with ultrasound frequency, the difficulty in fabricating the transducer arrays and electronic hardware is increased. This is because the size of the transduction elements become microscopic, and the required analog and digital frequencies of the electronic hardware increase.

Pulse-echo ultrasound imaging is a technique whereby short bursts of radio frequency (RF) sound are emitted and received from small electromechanical transduction elements, and the detected echoes are used to map the acoustic properties of the tissues from which the sound waves were reflected. Images are produced by assigning greyscale values to summed echo amplitudes and mapping the received information over the distance scanned.

The ability to focus and steer ultrasound energy during both transmission and reception is typically required to generate high quality high-resolution images. A one-dimensional array is made from a linear row of transduction elements. Each of these elements can be independently excited on transmit and digitized on receive. When the array is "beamformed", a time delay is applied to the excitation pulses for each element such that the wave-fronts constructively interfere along a line at a specific angle, and destructively interfere elsewhere.

Subsequently, the echoes that are received across the individual elements, can be digitally captured and delayed in order to create constructive interference on receive at a given steering angle. This provides a focused line of sight or "A-line". A full 2 D image is generated by collecting and plotting many parallel A-lines. Both transmit and receive beamforming are typically required in order to achieve a level of image quality required for most medical diagnostics. In a linear phased array transducer, a sector shaped image is generated in this way by changing the focusing delays for each angle. FIG. 1 illustrates geometrically how a 1D phased array steers and focuses the ultrasound beam throughout the azimuth (or lateral) direction.

High-frequency ultrasound is still a relatively new technology that uses micro-fabricated ultrasound transducers to achieve imaging resolution of a few tens of microns, an order of magnitude higher than conventional ultrasound imaging systems. By increasing the frequency, however, the wavelengths of the sound bursts are reduced and this causes increased attenuation of the signal limiting the applications to structures relatively near the face of the probe (i.e. ideal for endoscopy). On the electronic side, high-frequency ultrasound, typically defined as greater than 30 MHz, requires much higher analog-to-digital sampling rates and data capture rates. A generally accepted performance benchmark dictates that approximately 30 samples per wavelength are required to achieve adequate beamforming accuracy and image quality. If less than this many samples per wavelength are present, degradation in the quality of receive beamforming occurs due to the quantization of the digital samples.

FIG. 2 depicts this effect by illustrating the digitally quantized samples for two channels of the array after they have been captured by analog-to-digital-converters (ADCs). The receive delays that are inserted for channel "n" and "n-2" in this example, are chosen such that they attempt to realign the echoes between these two channels by compensating for the difference in time-of-flight (TOF) arrival time for the echo. Because the accuracy of aligning these pulses is limited to the quantization of the digital sample points, the pulses cannot be properly aligned and achieving perfect constructive interference between these elements is not possible.

When the frequency of the ultrasound is increased, obtaining enough samples per wavelength to avoid quantization error becomes increasingly more difficult because of the data sampling/transfer rates required. At high frequencies, for example, for a 50 MHz 64 element phased array, an effective sampling rate of 1.5 GHz would be required to achieve the 30 samples per wavelength benchmark. Given that the system uses 64 array elements and that each sample is typically 12 bits wide, the data capture rate for the system would therefore be 1.1 Tb/s or 140 GB/s. This is an incredibly high data capture rate and is equivalent to transferring 80 full length DVD quality movies every second. In practice, however, such a brute force approach would not be undertaken, not only because of the high data capture rate, but also because 64 parallel 12-bit 1.5 GHz ADC channels would likely be prohibitively expensive to implement in a commercial imaging system.

Conventionally, the approach taken at lower frequencies has been to digitize at approximately 4-15 times the ultrasound center frequency, and then subsequently up-sample by interpolating values in-between the actual data points captured [1], [2]. By up-sampling the waveforms to up to 30 samples per wavelength through interpolation, the pulses can then be digitally delayed with the required precision for quality beamforming [1]. There is a trade-off, however, between the processing power required and how many interpolated samples are needed between the actual data points. For example if digitization at 10-15× the center frequency is implemented, linear interpolation between sequential data points with only a small amount of processing power is required. If, however, one captures data at a much lower sampling rate, then non-linear convolution interpolation is required, which uses huge amounts of computing resources and makes real-time frame rates very difficult. In addition, even at the lowest reported sampling rates, a 50 MHz array would still need to be digitized at more than 200 MHz. Finally, since interpolating still results in 30 samples per wavelength, large amounts of unused data typically needs to be transferred to the host or a GPU, often limiting frame rates [3].

There has also been an alternative technique developed recently that allows one to avoid both prohibitively fast sampling/transfer rates and computationally intensive up-sampling. This technique is referred to as "compressed sensing" and avoids the requirement of fine sampling by inserting the beamforming delays in the frequency domain [4-6]. Although the data capture/transfer rate using this approach can be very low, an FFT is required for each element's RF signal prior to beamforming. Performing FFT's on 64 parallel RF signals also requires a significant amount of processing power to achieve real-time frame-rates. In addition, finely tuned analog filters are required for each channel on receiving the signals in order for this technique to work. This can introduce further phase delay errors due to channel to channel variations.

An alternative approach previously introduced both for low [7], [8] and high [9] frequency annular array transducers results in a very low data capture rate, and has minimal processing requirements. The technique is referred to as the "variable sampling" method of beamforming. With this technique, as the name suggests, the sampling rate is not constant, but is in fact independently varying with a different pattern for each ADC throughout the depth of the A-line. In a phased array transducer, these patterns change with steering angle as well. To determine the pattern of sampling, the round-trip TOF from the transmit pulse to a pixel location and then back to the individual array element, is pre-calculated by assuming a constant speed of sound.

FIG. 3A shows the TOF path for two elements in the array for pixel number 3 in a given A-line. If the ADC 'encodes' for the individual array elements are triggered exactly at the TOF path delay times, then the beamforming delays have in fact already been inserted before the digitization and thus this method avoids quantization errors. By collecting samples with the proper TOF path delays for each pixel depth, a focused A-line is generated by simply adding sequential samples across elements. It should be noted that the TOF path delay does not change with constant increments throughout the A-line, so the sampling rate is not constant throughout depth and it changes at a different rate for each element and steering angle.

FIG. 3A also illustrates that in fact two samples are captured per pixel with this technique and are referred to as in-phase (I) and quadrature (Q). Since phase information is required to demodulate the RF signal, 2 samples separated by ¼λ, are usually used in order to make demodulation computationally very fast. The envelope or Hilbert transform can be closely approximated by $\sqrt{I^2+Q^2}$ with minimal processing resources.

In order to create a two-dimensional (2-D) image, it is necessary to collect many adjacent A-Scans throughout the region of interest using the beamformers (or by mechanically stepping the transducer in the lateral direction). The electronic signal collected from each A-Scan is demodulated or envelope detected, in order to provide an amplitude map of the reflected energy. The envelope signal can be produced by rectifying and filtering the signal or by using a technique called quadrature sampling. The theoretical basis for this technique is described below. Most ultrasound images are displayed using a greyscale map, in which the amplitude of the envelope signal is coded as grey-level ranging from black (smallest signal) to while (largest signal). An example of a demodulated A-Scan and the corresponding greyscale map is shown in FIG. 3B. Historically the greyscale map was referred to as brightness mode or B-mode imaging. The idiom 'B-mode image', however, has evolved over the years to denote a 2-D collection of brightness mode A-scans.

In FIG. 3B, the received ultrasound signal v(t) is displayed along with the envelope function a(t). The signal v(t) can be represented by the envelope function multiplied with a carrier wave (equation 1).

$$v(t)=a(t)\cos(2\pi ft-\phi) \quad (1)$$

In equation 1, the cosine function is the carrier signal, with frequency f and relative phase ϕ. Equation 1 can be expanded using one of the fundamental trigonometric identities [16] to obtain:

$$v(t)=a(t)\cos(2\pi ft)\cos(\phi)+a(t)\sin(2\pi ft)\sin(\phi) \quad (2)$$

The frequency independent terms in equation 2 can now be grouped to form:

$$v(t)=I(t)\cos(2\pi ft)+Q(t)\sin(2\pi ft) \quad (3)$$

where I(t) is referred to as the in-phase signal component and Q(t) as the quadrature component. $I(t)$ and Q(t) are related to the envelope function a(t) according to:

$$a(t)=\sqrt{I(t)^2+Q(t)^2} \quad (4)$$

Since the demodulated envelope function a(t) is required in order to generate a B-mode image, equation 4 provides a means of obtaining the envelope by directly sampling the in-phase and quadrature signal components. These two orthogonal sine and cosine functions are weighted by the in-phase and quadrature components respectively.

Quadrature sampling conventionally involves spitting a signal between two channels, one of which is delayed by a quarter wavelength (¼λ) with respect to the other [17]. Since a sine wave is just a cosine wave delayed by ¼λ, the two signals provide the in-phase and quadrature components of v(t). This eliminates the dependence on ϕ and makes direct measurements of a(t) from v(t) possible.

FIG. 3C illustrates this method of envelope detection. By directly sampling the signal from each channel, the amplitude of the envelope can be determined by taking the square root of the sum of the squares (equation 4). This method of demodulation however, is only an approximation. Since the original pulse is broadband, a quarter wavelength delay is only accurate for the centre frequency of the pulse. All of the other frequency components are not delayed by exactly ¼λ, and so the 'I' and 'Q' components are not perfectly separated. Quadrature sampling is usually a good approximation, and is commonly used in commercially available systems.

SUMMARY

The present disclosure provides systems and methods for ultrasound imaging using a modified variable sampling beamforming technique. Unlike conventional methods of variable sampling beamforming, in which in-phase and quadrature samples are obtained for each pixel location, in various example embodiments of the present disclosure, the pixel locations are quadrature-spaced such that for each sample point, an adjacent sample point that approximately corresponds to an adjacent pixel location along an A-line is employed as the quadrature sample. In one example embodiment, the samples at each array element may be triggered according to the time of flight between a first pixel location and the location of the array element, such that successive samples, corresponding to successive pixel locations along the selected A-line, are obtained such that adjacent samples are spaced by a time interval corresponding to a quarter of an odd number of wavelengths of the beamformed transmit pulse, and such that only one sample is acquired per pixel. The systems and methods disclosed here may be employed to achieve high-frequency ultrasound imaging with a low number of sample acquisitions at a reduced data transfer rate.

Accordingly, in a first aspect, there is provided a method of performing ultrasound imaging using variable sampling beamforming, the method comprising:

transmitting a beamformed transmit pulse from an array of ultrasound elements along a selected A-line;

receiving, with the array of ultrasound elements, received ultrasound signals;

triggering sampling of the received ultrasound signals, for each ultrasound element, to obtain sampled signals at a plurality of sample times, each sampled signal corresponding to a respective pixel location along the selected A-line, wherein the first sample time along the selected A-line for a given ultrasound element, relative to its respective transmit time, is determined by calculating a round-trip time-of-flight delay between the given ultrasound element and a first pixel location on the selected A-line, and wherein successive samples, corresponding to successive pixel locations along the selected A-line, are obtained such that adjacent samples are spaced by a time interval corresponding to a quarter of an odd number of wavelengths of the beamformed transmit pulse, and such that adjacent samples have a temporal spacing suitable for sampling a pulse envelope of the beamformed transmit pulse;

for each pixel, combining the sampled signals from the array of ultrasound elements to obtain a beamformed sampled signal; and processing the beamformed sampled signals to generate a waveform associated with the selected A-line, wherein for each pixel, a respective quadrature value is obtained from the beamformed sampled signal associated with an adjacent pixel.

In another aspect, there is provided an ultrasound imaging system comprising:

an array of ultrasound elements;

a transmit beamformer operably coupled to said array of ultrasound elements;

a receive beamformer operatively coupled to said array of ultrasound elements;

the receive beamformer comprising computer hardware configured to:

trigger sampling of the received ultrasound signals, for each ultrasound element, to obtain sampled signals at a plurality of sample times for a plurality of A-lines, wherein for each ultrasound element and each A-line, each sampled signal corresponding to a respective pixel location along the A-line, and wherein the first sample time along the selected A-line for a given ultrasound element, relative to its respective transmit time, is determined based on a pre-programmed round-trip time-of-fight delay between the given ultrasound element and a first pixel location on the A-line, and wherein successive samples, corresponding to successive pixel locations along the selected A-line, are obtained such that adjacent samples are spaced by a time interval corresponding to a quarter of an odd number of wavelengths of the beamformed transmit pulse, and such that adjacent samples have a temporal spacing suitable for sampling a pulse envelope of the beamformed transmit pulse;

wherein the receive beamformed signal is further configured to:

combine, for each A-line, the sampled signals from the array of ultrasound elements to obtain a beamformed sampled signal for each pixel of each A-line; and process the beamformed sampled signals to generate a waveform associated with each A-line, wherein for each pixel, a respective quadrature value is obtained from the beamformed sampled signal associated with an adjacent pixel.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
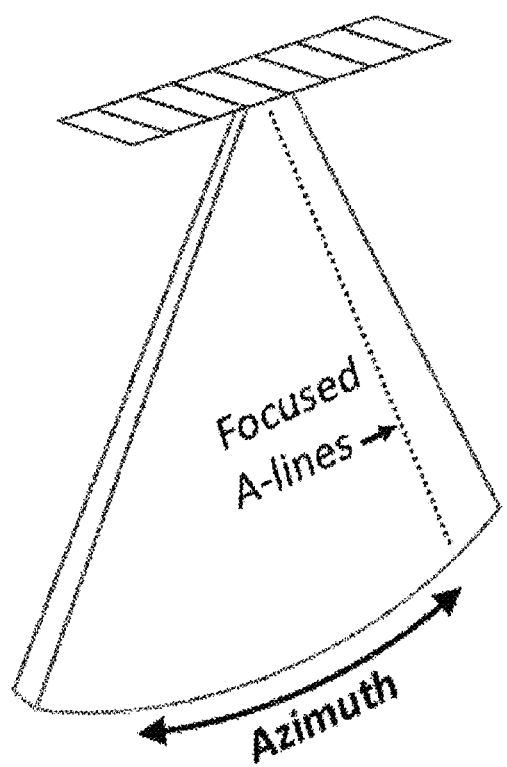
FIG. 1 illustrates a phased array sector scan.
Figure 2:
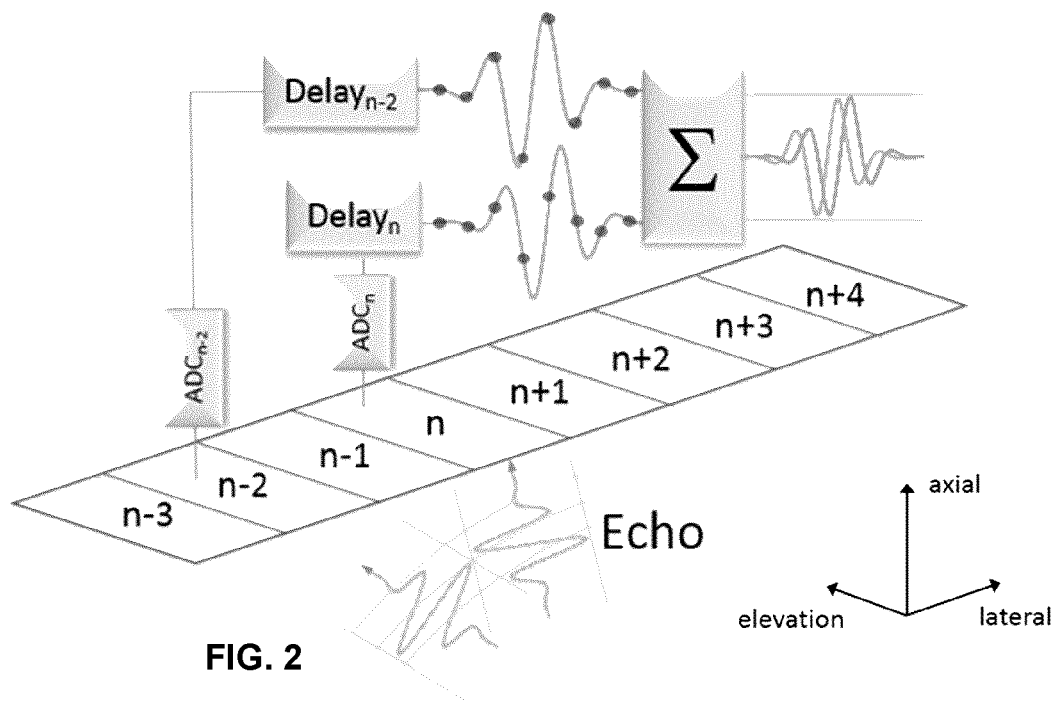
FIG. 2 is an illustration of the sampling of received signals from an array of ultrasound elements, showing delay quantization errors.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the phrase "wavelength", when referring to a pulse, refers to any wavelength within a bandwidth associated with the pulse. For example, the phrase "wavelength" may refer to the center wavelength of a pulse, or, for example, a wavelength within a −3 dB or −6 dB pulse bandwidth, or any other suitably defined pulse bandwidth.

Although the variable sampling technique, as described above, inherently provides a low data and low processing requirements, controlling these constantly changing sampling patterns for each element/depth/steering angle, with the required sub-nano second precision, introduces many design challenges. In addition, the "¼λ quadrature" sampling introduces constraints on the lower limit of ADC sampling rate. For example, in the case of a 50 MHz array, a lower ADC sampling limit of 200 MHz would be required. Unfortunately, ADC converters with 200 MHz sampling capability are presently very expensive, especially when >64 are required in the Beamformer. In the previous high-frequency implementation [9], the high sampling rate issue was avoided by implementing two ADCs per channel, one for "I" and one for "Q". This design is suitable for a low element count annular array, however, for a phased array with >64 elements, it becomes bulky, expensive, and twice as many ADCs and FPGA IOs are required for data capture.

Figure 3A:
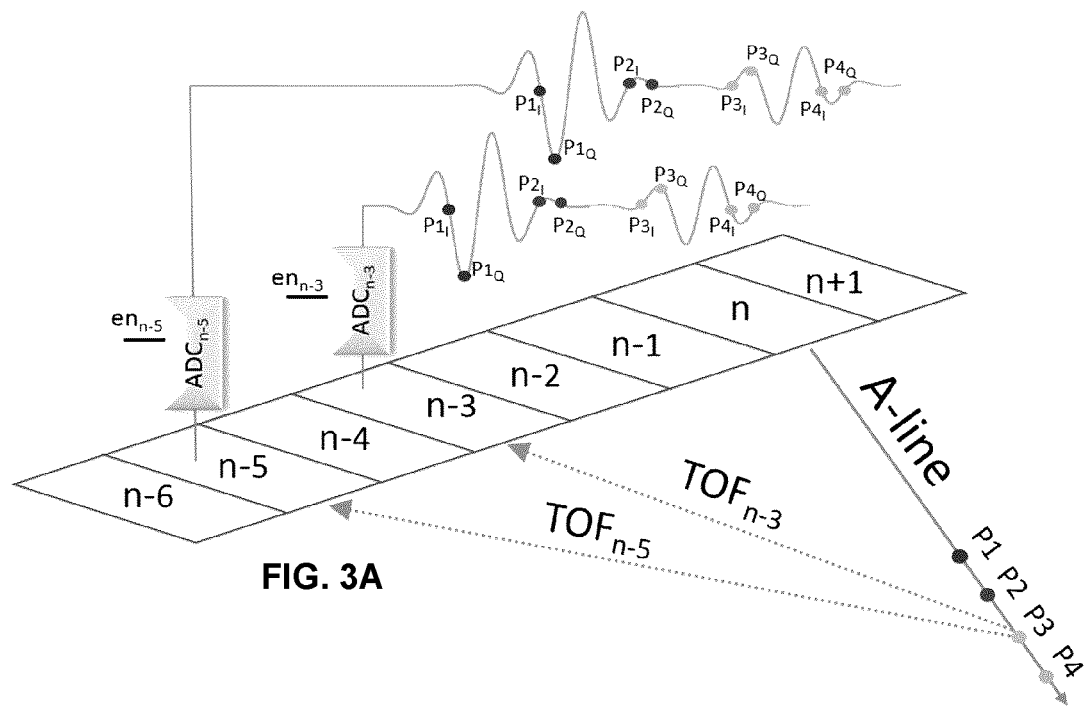
FIG. 3A illustrates the variable sampling beamforming method.
Figure 3B:
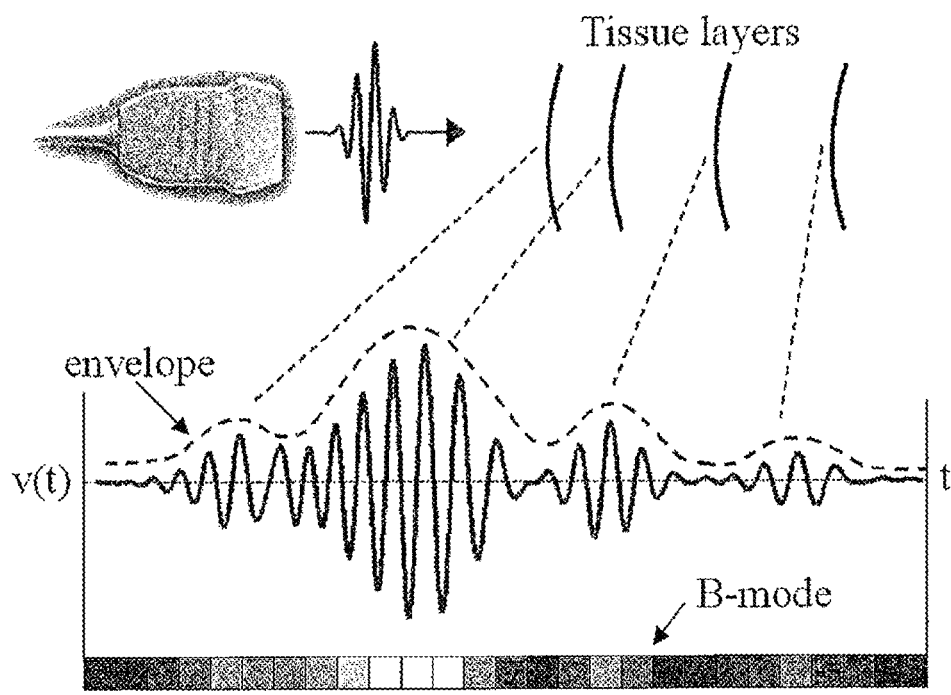
FIG. 3B illustrates envelope detection. The recorded echo signal requires rectifying and filtering before the amplitude can be mapped to a line of grey scale pixels. The brightness-mode (B-mode) line constitutes one line in a 2-D tissue image.
Figure 3C:
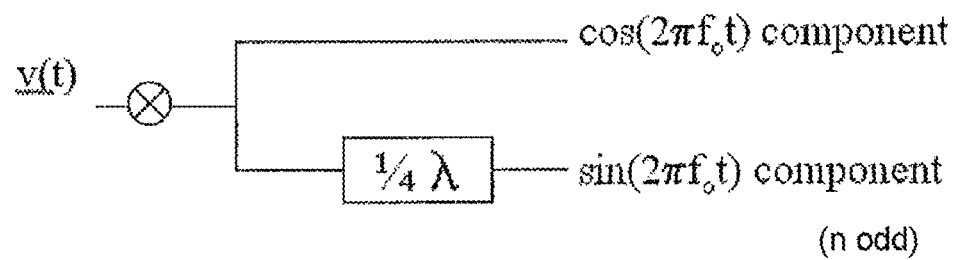
FIG. 3C illustrates the conventional quadrature sampling method of envelope detection. The original signal v(t) is split into two channels that differ in phase by ¼λ. This separates the in-phase and quadrature components.

As can be seen from FIG. 3A, the I-Q separation for adjacent samples can be different than the Q-I separation with the variable sampling technique. While the I-Q separation is fixed at ¼λ, the pixel separation (I-I separation) is chosen based on the bandwidth/response of the transducer. This is intentionally done in order to minimize any unnecessary data collection (one I/Q pair per pixel). Typically, the pixels are spaced approximately half the axial resolution (where axial resolution is defined as the full width half maximum (FWHM) of the pulse echo envelope). For example, if an endoscope has an axial resolution of approximately 50 microns, a pixel spacing of approximately 25 microns is required.

Various example embodiments of the present disclosure provide improved variable sampling systems and methods of beamforming that are capable of achieving a lower sampling rate, and lower processing requirements, than in conventional beamforming.

Figure 4A:
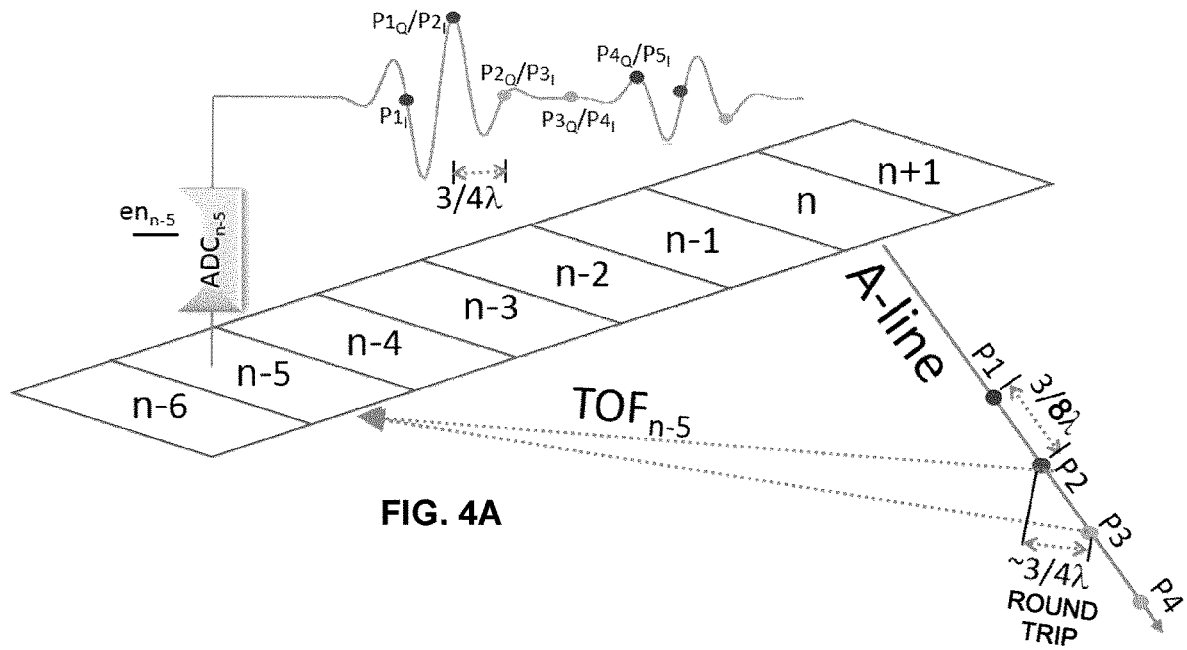
FIGS. 4A and 4B shows of the example ¾λ "one sample per pixel" method.

In one illustrative and non-limiting embodiment, sequential pixels are spaced along any given A-line (image line) such that time delay between samples associated with adjacent pixels corresponds to ¾λ, as shown in FIG. 4A. Samples are collected at the round trip TOF for each pixel-to-element. However, unlike the conventional variable sampling method described above, the ¼λ quadrature samples are not acquired for each pixel, and instead each successive sample (pixel) is employed as both the quadrature (Q) sample and the in-phase sample (I) for the next pixel, such that a single sample is obtained for each pixel location. Provided that the FWHM of the pulse envelope is sufficiently large relative to the sampling interval, the sampled signal can be demodulated with ¾λ spaced I-Q samples in place of ¼λ. In one example implementation, the envelope may be larger than two times ⅜λ, such that there is a small variation in envelope over the ⅜λ spacing. The pulse envelope can be defined, for example, based on the −3 dB points, −6 dB points, or any other suitable method (e.g. based on pulse bandwidth).

Figure 4B:
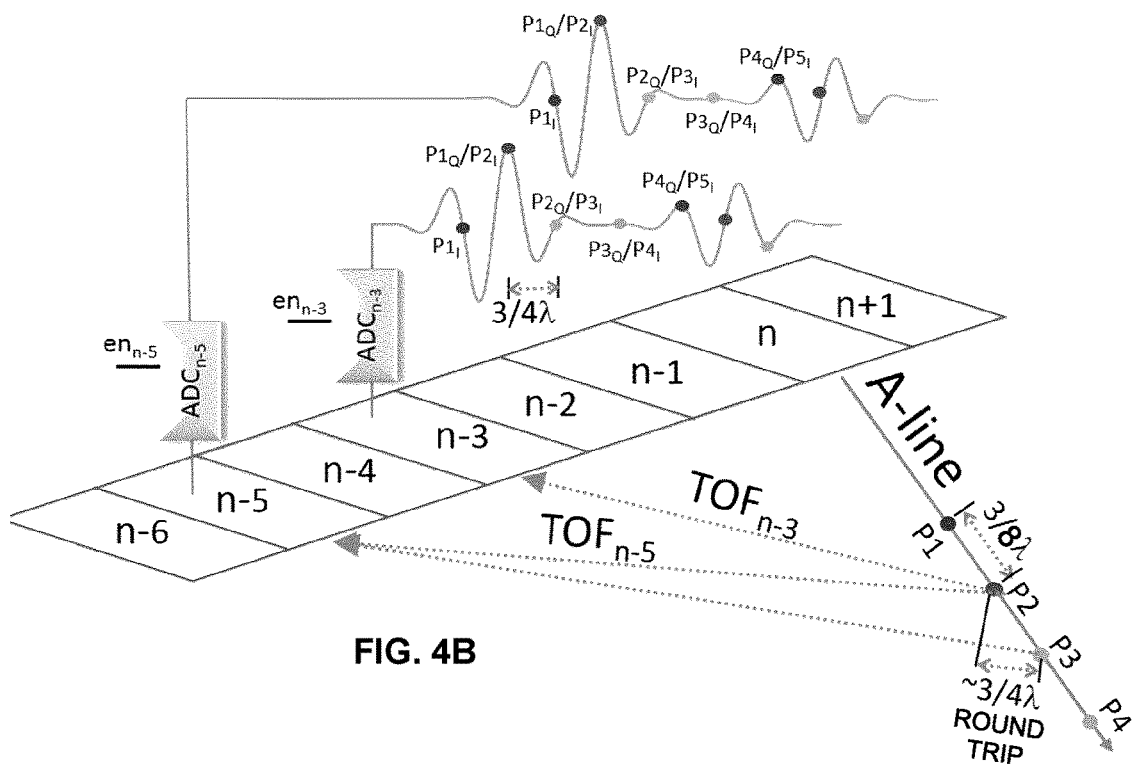

FIG. 4B shows the alignment of the sampling between different elements, such that quantization errors are not appreciably produced upon summation during beamforming.

FIG. 4B also shows that when the samples are obtained based on an adjacent pixel spacing, along the A-line, of ⅜λ, the actual time round-trip delay between adjacent samples closely approximates ¾λ. The approximation for the round-trip TOF being ¾λ becomes worse for elements farther from the center of the array, at larger steering angles, as well as for shallower depths (lower f-numbers). Therefore, in some embodiments, the temporal spacing between adjacent samples can be ¾λ, such that the spacing of adjacent pixels approximately equals ⅜λ.

In one example application, using the example phased array endoscope, the error in the approximation of ¾λ roundtrip TOF difference between successive pixels ranges between only +/−1.4% for the worst case scenario of farthest element from A-line (el1 or el64), largest angle (+/−40 deg), and lowest f-number (f-1.8). This small error in I-Q demodulation will not have a noticeable effect on the detection of the A-line envelope.

The present example method can be beneficial in reducing the processing requirements and cost of an ultrasound imaging system. Not only does the example method cut the total amount of data captured in half, but it also allows for lower frequency ADCs to be used for the I-Q samples. For example, since samples are only collected a times corresponding to every $3/4\lambda$. (or more generally, an odd multiple of $1/4\lambda$, as described below) the required average sampling rate for a 50 MHz array is 50/0.75-66.7 MHz. Therefore, without loss in image quality or resolution, this example method requires only one sample per pixel to be collected (per element) and cuts the ADC sampling frequency to $1/3$rd. It is noted that it would be virtually impossible to achieve equivalent image quality or resolution by collecting less than 1 sample per pixel, or spacing the pixels more coarsely (since $3/8\lambda$ pixel spacing is half of the axial resolution in the present example).

Although FIGS. 4A and 4B illustrated an example embodiment in which the sequential spacing between adjacent pixels is $3/8\lambda$, it will be understood that this was but one example, and that in other embodiments, different spacings may be employed, provided that the spacing is sufficient for sampling the pulse envelope.

Figure 5A:
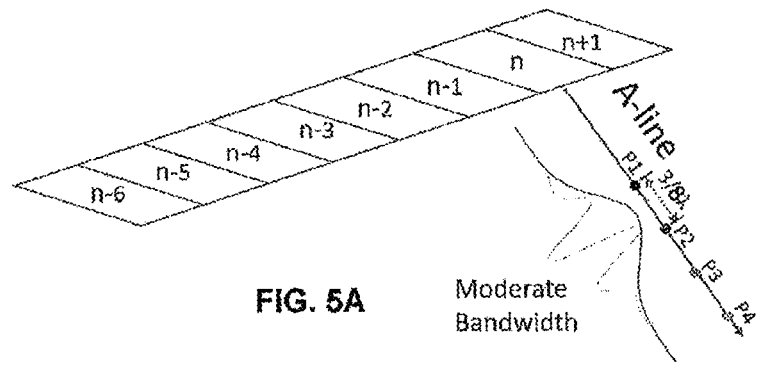
FIGS. 5A-C illustrate different sampling configurations that depend on the relative bandwidth of the transmit pulses.
Figure 5B:
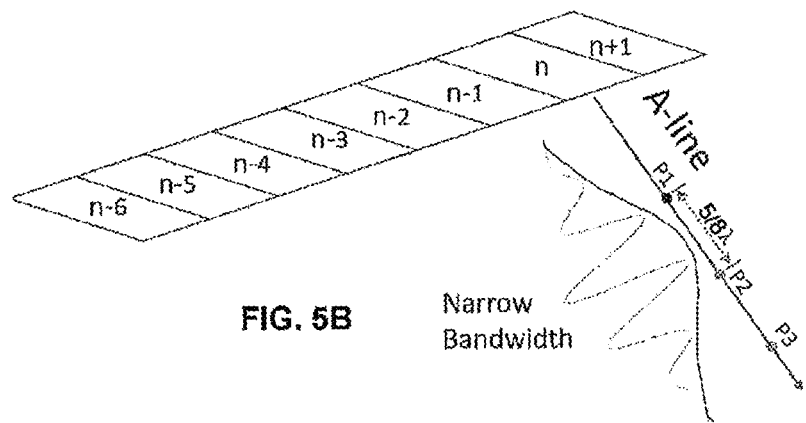
Figure 5C:
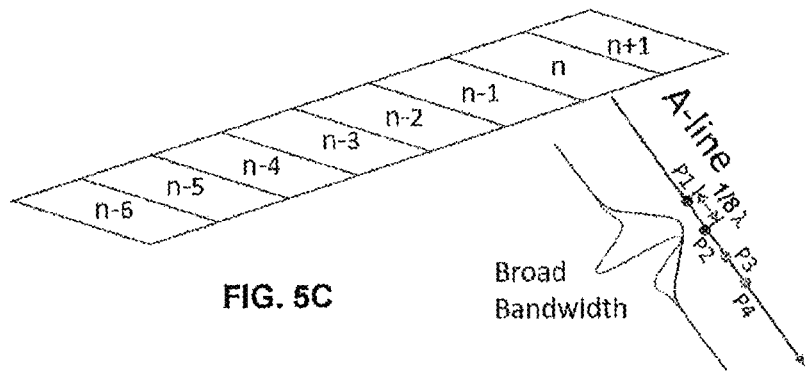

Some representative, yet non-limiting, examples are illustrated in FIGS. 5A-C, which show the use of pixel spacings of $3/8\lambda$, $5/8\lambda$, and $1/8\lambda$ (corresponding to sampling intervals of $3/4\lambda$, $5/4\lambda$, and $1/4\lambda$, respectively, for pulses having a moderate, narrow, and broad bandwidth, respectively, such that in each case, the spacing is sufficiently small to sample the pulse envelope, such that the pulse envelope can be reconstructed upon demodulation. In each case, samples are collected at the round trip TOF for each pixel-to-element. However, unlike the conventional variable sampling method described above, the quadrature samples are not acquired for each pixel, and instead each successive sample (pixel) is employed as both the quadrature (Q) sample and the in-phase sample ( ) for the next pixel. Example 3 and FIG. 16 of the present disclosure provide simulation results comparing the envelope amplitude loss (quantified as the maximum envelope estimation error) between samples for $1/4$, $3/4$ and $5/4\lambda$ sampling as a function of bandwidth.

Figure 6A:
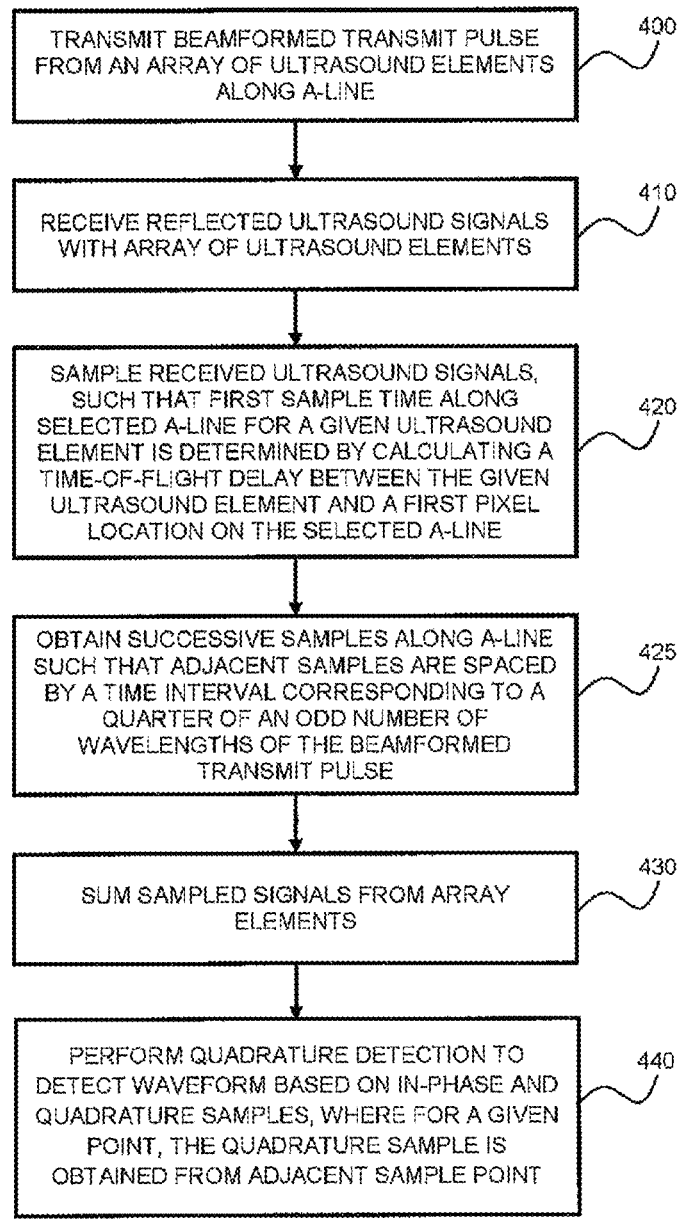
FIG. 6A is a flowchart illustrating a method of variable sampling beamforming using the "one sample per pixel" method.

FIG. 6A is a flow chart illustrating an example method for performing beamforming using the present modified variable sampling beamforming approach. In step 400, a transmit pulse is beamformed and transmitted from an array of ultrasound elements along an A-line (image line). The reflected acoustic signals are received by the array of ultrasound elements in step 410, such that a received signal is obtained for each element.

In step 420, the received signals are sampled from each ultrasound element. The sampling is performed such that each sampled signal corresponds to a respective pixel location along the selected A-line. The first sample time along the selected A-line, for a given ultrasound element, is determined by calculating a time-of-flight delay between the given ultrasound element and a first pixel location on the selected A-line. As shown at 425, successive samples, corresponding to successive pixel locations along the selected A-line, are triggered such that adjacent samples are spaced by a time interval corresponding to a quarter of an odd number of wavelengths of the beamformed transmit pulse. The adjacent samples have a temporal spacing suitable for sampling a pulse envelope of the beamformed transmit pulse.

The time of flight delays for each element and each pixel location may be pre-calculated. This sampling based on time-of-flight eliminates the need to insert beamforming delays. The sampled signals from the array elements are then summed, as shown at step 430.

In step 440, waveform detection is then performed using a quadrature detection, where, for a given sample point (corresponding to an in-phase sample point), the quadrature sample is obtained from an adjacent sample point, without the need to separately sample a quadrature sample point. This method may be repeated at multiple A-lines to form a two-dimensional image.

Figure 6B:
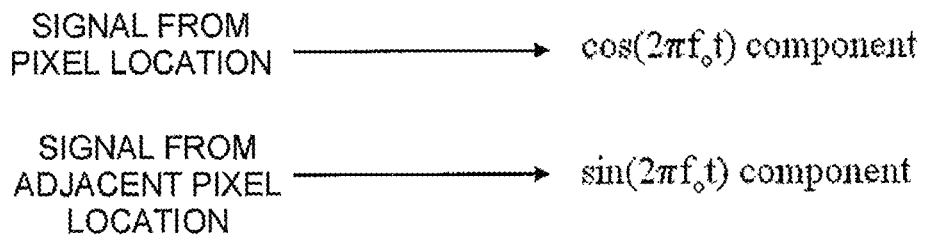
FIG. 6B illustrates the conventional quadrature sampling method of envelope detection. The signal for a given pixel, and the signal from an adjacent pixel, are employed as the in-phase and quadrature components, respectively.

As noted above, quadrature sampling can also be obtained for phase delays other than $1/4\lambda$, where the phase delay may be more generally expressed as $n\lambda/4$, where n is odd (e.g. additional delays or phase offsets include $3/4$ lambda, 1.25 lambda, 1.75 lambda, etc.). Such other phase delays also result in the orthogonal (quadrature) component (theoretically for a single frequency wave). FIG. 6B illustrates this method of envelope detection.

The aforementioned example embodiment is involves sampling and envelope detection based on a separation of an odd number of quarter wavelengths between adjacent pixels. It will, however, be understood that in other embodiments, other pixel separations may be employed.

Figure 7:
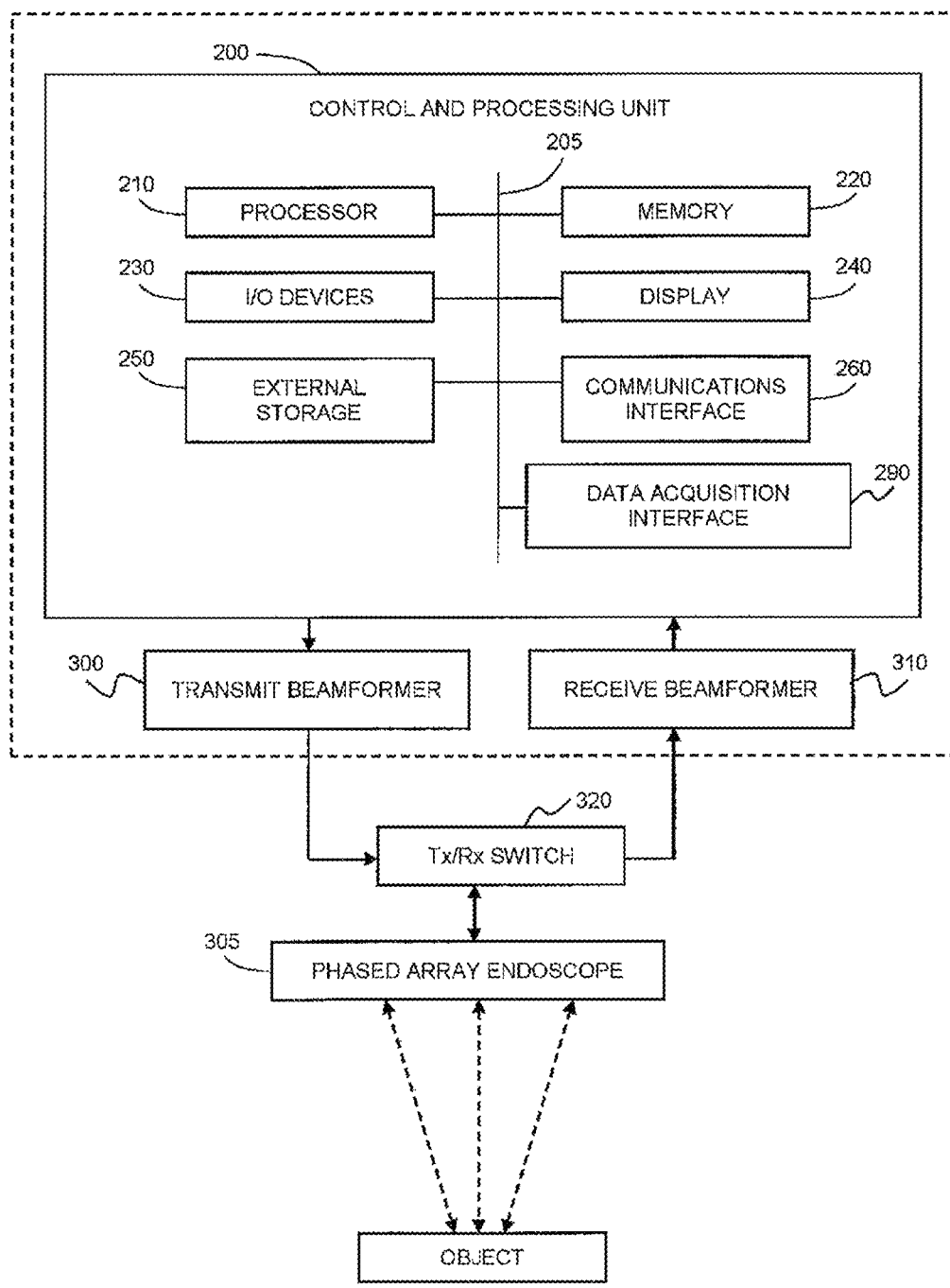
FIG. 7 is an example of an endoscopic imaging system for implementing embodiments of the present disclosure.

Referring now to FIG. 7, an example endoscopic imaging system for performing the methods described above is illustrated. The example system includes the following components:

1) A phased array endoscope 305 (e.g. 50 MHz, 64 element);

2) a transmit beamformer 300 with pulser-receiver circuitry 320 (e.g. 50 MHz, 64 element);

3) a receive beamformer 310 (e.g. 50 MHz, 64 element); and 4) a control and processing unit 200 (e.g. a controller, computer, or computing system). The control and processing unit may include and execute scan conversion software (e.g. real-time scan conversion software).

Figure 8:
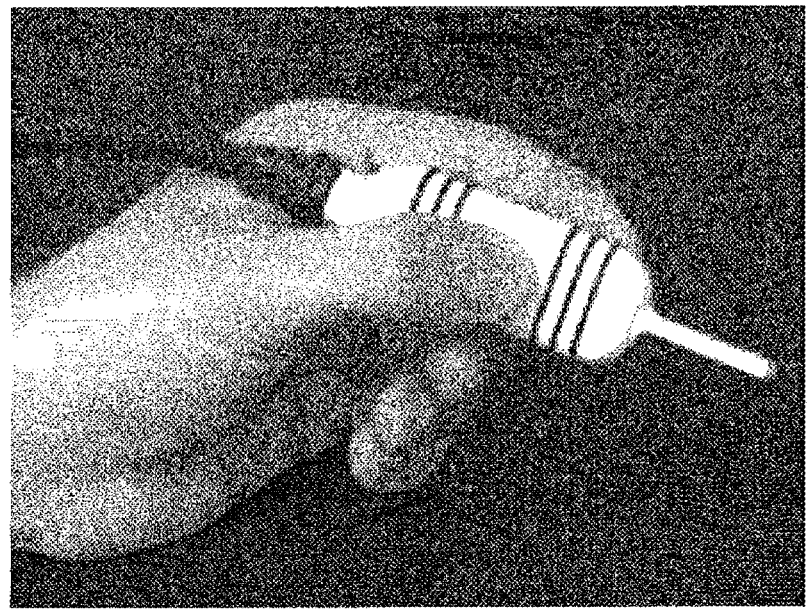
FIG. 8 is a photograph of a packaged endoscope.

An example of a phased array endoscope 305 is disclosed in [10], [11]. Briefly, the example endoscope includes a high-resolution linear phased array operating at very high frequency (40-50 MHz). As linear phased array transducers have the advantage of generating a large field-of-view from a small aperture, such a high-frequency phased array has also been packaged into a miniaturized endoscopic form factor (<3 mm in cross-sectional dimensions) in order to make it suitable for minimally invasive clinical procedures. The development of this probe has overcome many challenges associated with the micro-fabricating and packaging of 64 microscopic transmitter-receiver elements into such a small area. A high-resolution endoscope such as this one has many potential endoscopic applications such as, but not limited to, laparoscopic, auditory, neural, intracardiac imaging [12-15], pre-natal imaging, renal imaging, and urethral imaging. In these applications the technology confers the benefits of reducing the number of samples that need to be acquired and processed in order to obtain an image and reducing the cost of the ADCs. FIG. 8 shows a photograph of a packaged 64-element endoscope.

In one example implementation, a receive beamformer suitable for real-time imaging may be provided according to the following design criteria. First, by implementing the 'one sample per pixel' variable sampling technique as described above, creating unique variable delay patterns for all 64 elements, and ~100 steering angles requires that the accuracy of the ADC sampling clocks be sub-nanosecond.

For example, if 512 pixels are used in the depth direction (3-10 mm with ⅜λ pixel spacing), then the number of precisely timed ADC clock triggers required for 128 unique imaging angles is 64*512*128=4.19M. This can be achieved, for example, using a next generation field programmable gate array (FPGA) that can achieve the required ADC sampling patterns (clock triggers).

The second design criterion for the example receive beamformer is capturing the data in parallel. Although the average sampling rate using the aforementioned method is significantly relaxed (e.g. a sampling rate of ~65 MHz can be achieved using ¾λ sampling), a high data capture rate is still required (e.g. 65 MHz*12 bits wide*64 channels=6.4 GB/s for the example sampling rate of 65 MHz).

Accordingly, in one example implementation, the receive beamformer may include:

1) a mother board with an on-board FPGA that is capable of generating the variable ADC clock triggers for 64 channels and 128 steering angles;

2) a modified version of an 8 channel data acquisition card that will plug into the mother board, accept the variable clock triggers, and capture the data at rates up to 1.5 GB/s; and 3) additional 8 channel data acquisition cards that will plug into the mother board and bring the data capture rate up to, for example, 12 GB/s (e.g. more than the aforementioned 6.4 GB/s using the 'one sample per pixel' technique).

Figure 9:
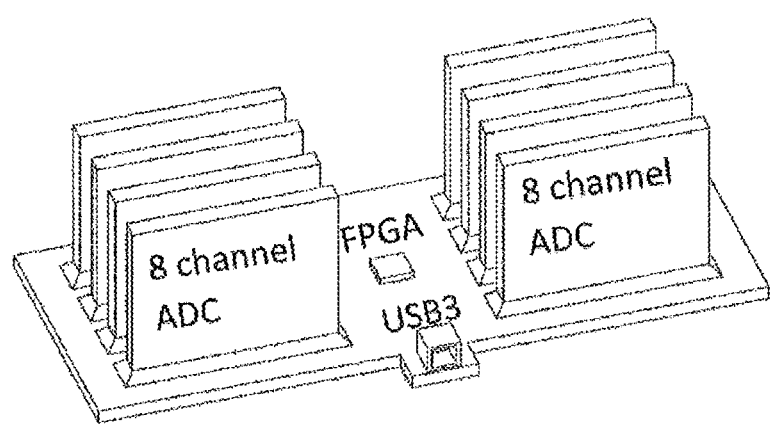
FIG. 9 is a diagram of an example receive beamformer with motherboard and 8×ADC daughter boards.

FIG. 9 illustrates an example implementation of the integration of 9 circuit boards to complete an example 64 channel variable sampling receive beamformer. Such a high frequency, miniaturized (e.g. <3 mm is cross-sectional dimensions) imaging endoscope and associated electronic hardware and software can enable this technology to be used as a tool for visualizing tissues from within the body, as opposed to the current equivalent technology that is limited to external topical applications. Potential applications of such a high resolution endoscope include laparoscopic, auditory, intracardiac, neural imaging, and many more. Currently no other ultrasound technology exists that combines such high resolution, with the miniature forward looking endoscopic form factor.

Referring again to FIG. 7, a control and processing unit 200 is employed to control transmit beamformer 300 and receive beamformer 310, and to process the beamformed signals.

As shown in FIG. 7, in one embodiment, control and processing unit 200 may include a processor 210, a memory 220, a system bus 205, one or more input/output devices 230, and a plurality of optional additional devices such as communications interface 260, data acquisition interface 290, display 240, and external storage 250.

It is to be understood that the example system shown in the figure is not intended to be limited to the components that may be employed in a given implementation. For example, the system may include one or more additional processors.

One or more components of control and processing unit 200 may be provided as an external component that is interfaced to a processing device. For example, as shown in the figure, transmit beamformer 300 and receive beamformer 310 may be included as a component of control and processing unit 200 (as shown within the dashed line), or may be provided as one or more external devices. Transmit beamformer 300, receive beamformer 310 and image processing engine 280, may be configured or programmed to execute algorithms for performing the methods described herein.

Embodiments of the disclosure can be implemented via processor 210 and/or memory 220. For example, the functionalities described below can be partially implemented via hardware logic in processor 210 and partially using the instructions stored in memory 220. Some embodiments are implemented using processor 210 without additional instructions stored in memory 220. Some embodiments are implemented using the instructions stored in memory 220 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

The forthcoming section of the present disclosure describes various example implementations employing computer hardware, such as application specific integrated circuits (ASICs) and field-programmable gate arrays (FPGAs) for performing receive beamforming (and optionally additional functions, such as transmit beamforming and additional signal processing) according to the aforementioned variable sampling methods.

As noted above, generating variable sampling patterns with sub-nano second precision is quite challenging on a high-frequency phased array system. For example, in the case of a 64 channel system using 512 pixels per A-scan line and 128 image lines (A-lines), a total of 4,194,304 sampling times must be pre-calibrated. In order to meet the system requirements a parallel platform must be utilized which is capable of dynamically controlling the sampling times during acquisition. Unfortunately, requiring that 4,194,304 sampling times be pre-calibrated into the system produces another inherent problem, high resource utilization. ASICs and FPGAs have limited resources and given the high resource demand of the variable sampling method, a low resource utilization solution is highly attractive. Furthermore sub-nano second sampling precision adds timing problems to high congestion and high fanout environments. Therefore in the interest of meeting system requirements it is desirable for the system architecture to have: relatively low chip congestion, reduced number of high fanout nets, and dynamically reconfigurable delays.

Previous work on variable sampling architectures include voltage controlled oscillators (VCOs) and the Flip-Flop chain model. Firstly, VCO clock control requires adjusting the control voltage to dynamically adjust the position of each successive rising edge. This method may be employed for low-frequency ultrasound, where the spacing of each successive sample is an order of magnitude larger than that of high-frequency ultrasound system. However, in the case of a high-frequency system, it would be practically impossible to accurately control the VCO voltage in the required time, rendering this method incapable of dynamically adjusting the A/D clocks for this application.

One may also consider the use of the Flip-Flop chain method for producing the precise timing required for a high-frequency phased array system. This method has previously been used on high-frequency annular array systems where each element focuses along one line only. However, unlike an annual array system, a phased array system must focus along many image lines to generate adequate images, thus many Flip-Flop chains would be required, or a plurality of multiplexers and/or logic gates would be required to generate the outputs. These drawbacks would require a drastic and highly impractical number of resources from the FPGA/ASIC platform, and would likely be impossible to implement using existing hardware. Furthermore the increase in output logic used for the increased number of image lines would drastically increase the data path delays within the FPGA, and this would likely create a plurality of timing issues.

In contrast to the variable sample methods employed in the past, the methods and devices described herein are suitable for implementing a variable sampling method using computer hardware such as a FPGA and or an ASIC architecture. As described in further detail below, the present example embodiments provide an improvement of the previous variable sampling implementations, as they achieve a reduction in the number of on-chip resources, while preserving timing resolution. This is achieved by implementing a high-frequency finite state machine architecture with supporting peripherals.

The present example embodiments may be implemented using computer hardware such as one or more ASICs or FPGAs, which employ topologies that provide the ability to provide customizable, modular, and parallel architectures capable of supporting each individual channel.

According to one example implementation, the computer hardware is configured to individually address the sampling times of each channel with a separate counter and state machine, where the counter is employed for generating a coarse delay, and the state machine is employed for controlling fine delay, in order to generate trigger pulses for sampling. This implementation reduces the need for high fanout nets connected to a global counter, as well as global timing control for channel synchronization.

Figure 10:
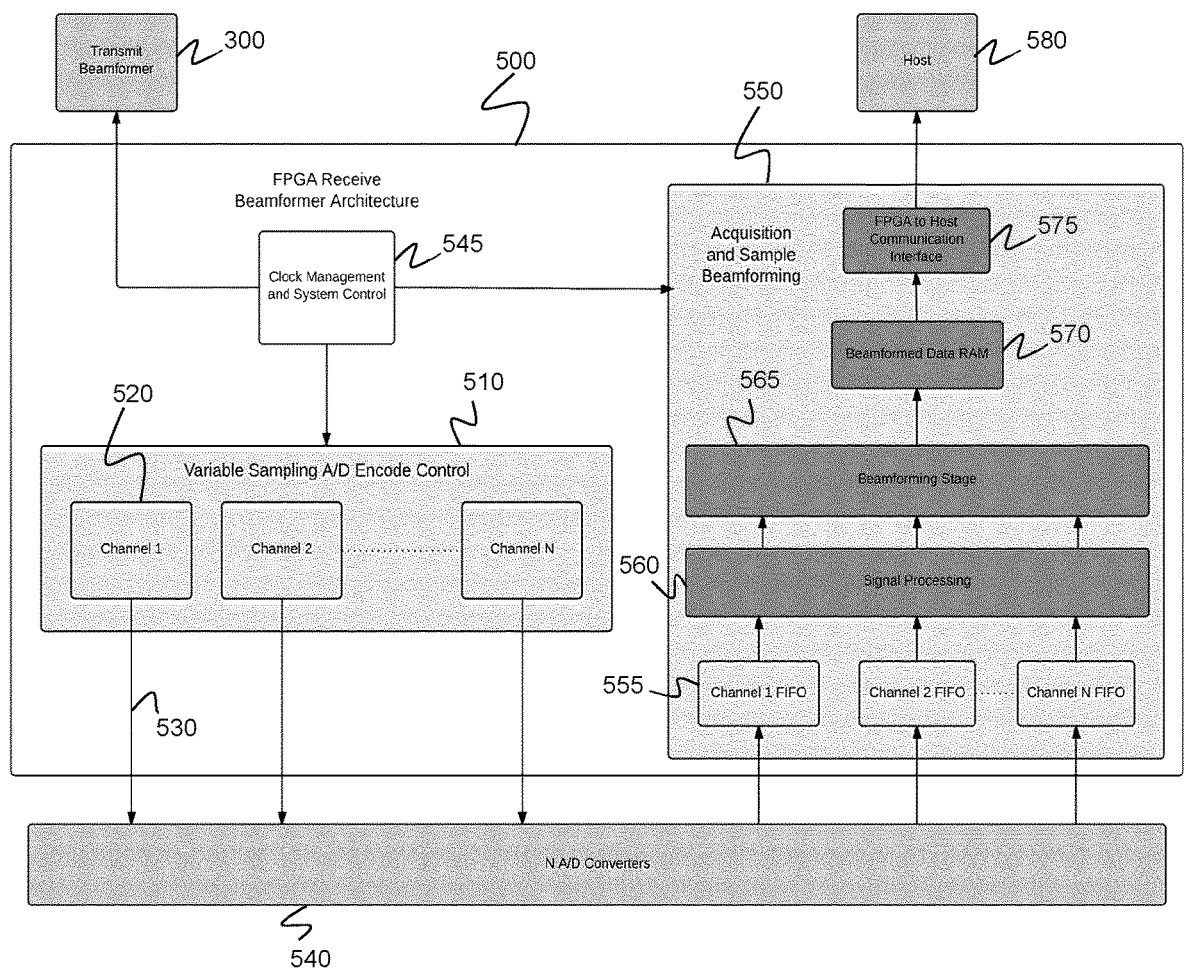
FIG. 10 schematically illustrates an example FPGA architecture for performing the beamforming according to the methods disclosed herein.

An example implementation of the system, shown in the non-limiting case of an FPGA implementation, is shown in FIG. 10. The FPGA 500 architecture includes a network of variable sampling encode controllers 510, with each variable sampling encode controller dedicated to a given channel 520 (ultrasound element). The output sampling clocks 530 are connected to external hardware with suitable analog-to-digital (A/D) converters 540.

The FPGA architecture 500 includes a clock management and system controller 545 that manages system clocks used by both the variable sampling encode control units 510 and the acquisition/beamforming portion 550 of the design. The output clocks 530 used for the variable sampling A/D encode control are derived from the same clock domain in order to prevent asynchronous timing problems throughout the FPGA architecture 500. The acquisition and sample beamforming portion 550 may run asynchronously with respect to the variable sampling A/D encode control, but this may not be preferable in the interest of implementation complexity.

The external A/D converters 540 provide data which will be acquired, for example, by a set of first-in-first-out (FIFO) memory modules 555. It will be understood that the disclosure is not intended to be limited to FIFO modules, other memory blocks, such as dual-port RAM, may also or alternatively be employed.

Acquired samples may optionally be processed through a digital signal processing unit (DSP) 560 for signal improvement. System DSP may be derived from FPGA DSP primitives or through fundamental components, whereby their application may include, but is not limited to, filtering, apodization, log compression, Doppler, and phase coherence weighting.

Processed data is then beamformed, via beamforming stage 565, before being stored into a RAM or memory unit. It is noted that additional signal processing may be applied to post-beamformed data. At this stage, the data is ready to be transferred to a host (e.g. a PC, or other computing system, such as the control and processing unit 200 shown in FIG. 7) through an interlace 575 which meets the system data and frame rate requirements.

Figure 11:
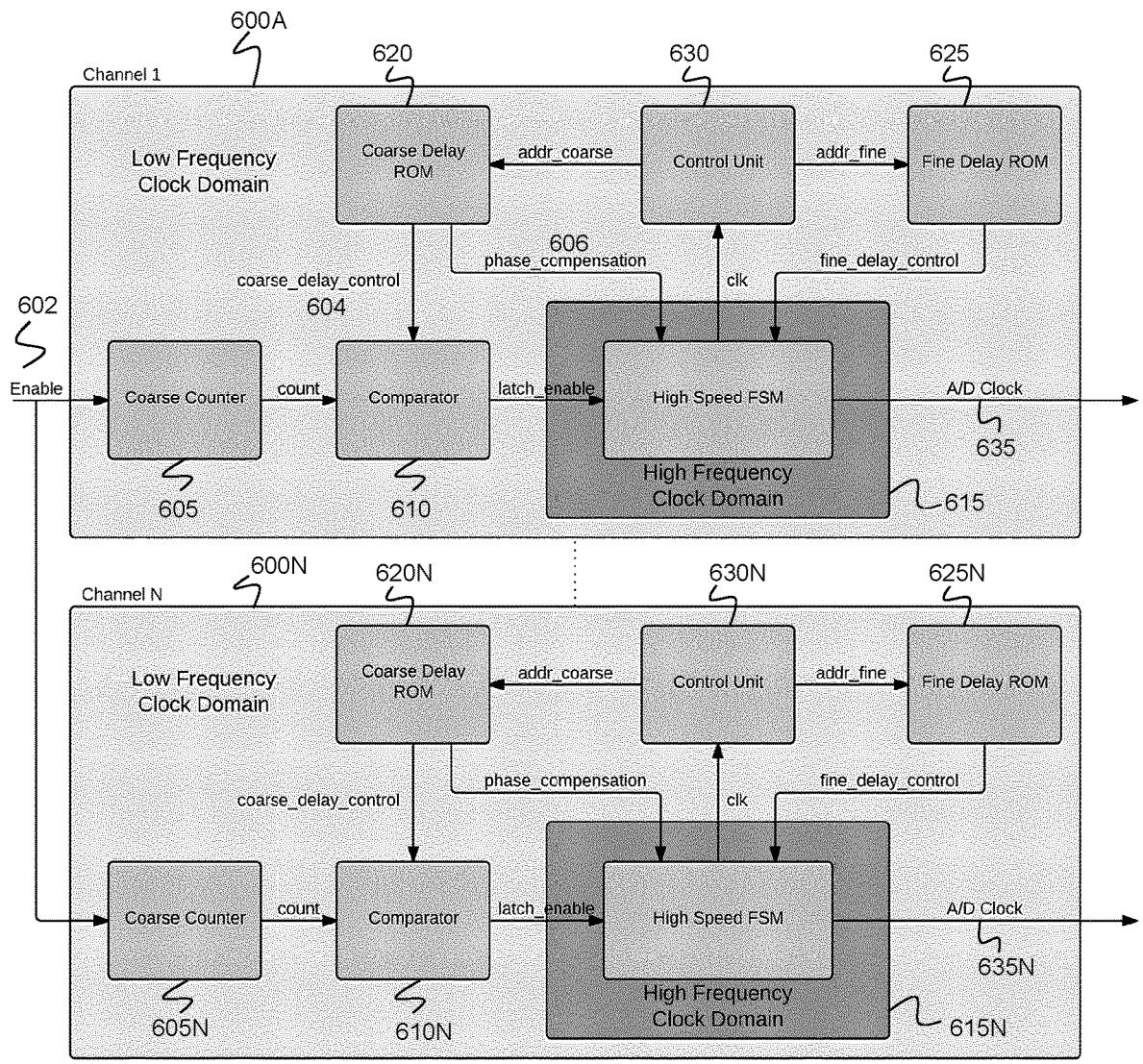
FIG. 11 shows an example implementation of an architecture of a variable sampling A/D encode controller that employs using a low-frequency counter and a high-frequency state machine.

The example implementation described herein primarily encompasses the receive beamformer (component 310 of FIG. 7) and the data path for the measured signals. Additional components are shown, for example, in FIG. 7. It will be understood that the external A/D converter 540 is connected to or connectable to an ultrasound probe, or more broadly, a sensor unit or network. As shown in FIGS. 8 and 11, a synchronized transmit beamformer 300 is employed for ultrasound applications. Alternatively, the transmit beamformer 300 can be integrated onto the same FPGA as the receive beamformer for a more compact or integrated design.

Referring now to FIG. 11, an example implementation of an architecture of a variable sampling ND encode controller that employs using a low-frequency counter and a high-frequency state machine is shown. As shown in the figure, each controller 600 . . . 600N is associated with a unique channel of the sensor array (e.g. a unique ultrasound array element). According to the present example implementation, the modules of each controller (for each channel) include: a low-frequency counter 605, a comparator 610, a high-speed finite state machine 615, a coarse delay ROM 620, a fine delay ROM 625, and a control unit 630.

The example variable sampling ND encode controller is configured or programmed to operate as follows, on a per-channel basis. Once enabled as shown at 602, the coarse low-frequency counter 605 controls the coarse delays for the round-trip time of flight between transmit events and the first receive sample for each mage line (each A-line) for its respective element. The output of the counter 605 is incremented with respect to the low frequency clock (not shown) and is compared to pre-calculated coarse delays. Once the counter reaches a pre-selected count value associated with the time-of-flight delay, the high-speed finite state machine 615 is initiated. As described below, the high-speed finite state machine 615 cycles between a controlled number of successive states, with each transition between states having a quantized fine delay associated therewith, and a trigger pulse 635 is generated at the completion of each cycle. The control over the number of states implemented per-cycle by the high-speed finite state machine may be implemented on a per-channel, per A-line, and per-pixel basis. As described below, the time delay associated with each cycle of states of the high-speed finite state machine may be controlled such that it equals a suitable time delay for variable sampling, within the quantization error associate with the high-speed finite state machine.

In the present example implementation, the comparison to the pre-calculated coarse delay is performed using a comparator 610. When the value of counter 605 matches the current data from the coarse delay ROM (shown as "coarse_delay_control" 604 in FIG. 11), the high-speed finite state machine 615 is initialized to begin sampling.

In order to preserve timing accuracy, the high-speed finite state machine 615 may be configured to compensate for relative timing errors between the low-frequency counter and the high-sped finite state machine, such as the clock domain crossing between the low-frequency counter and the high-speed state machine. For example, a phase compensation value for implementing a phase compensation delay using the high-speed finite state machine may be pre-calculated and stored (for example, in the coarse delay ROM 620 along with the coarse delays). The phase compensation may be applied for the first sample of each image line (A-line), on a per-element basis, by skipping a prescribed number of states within the high-speed finite state machine.

Figure 17:
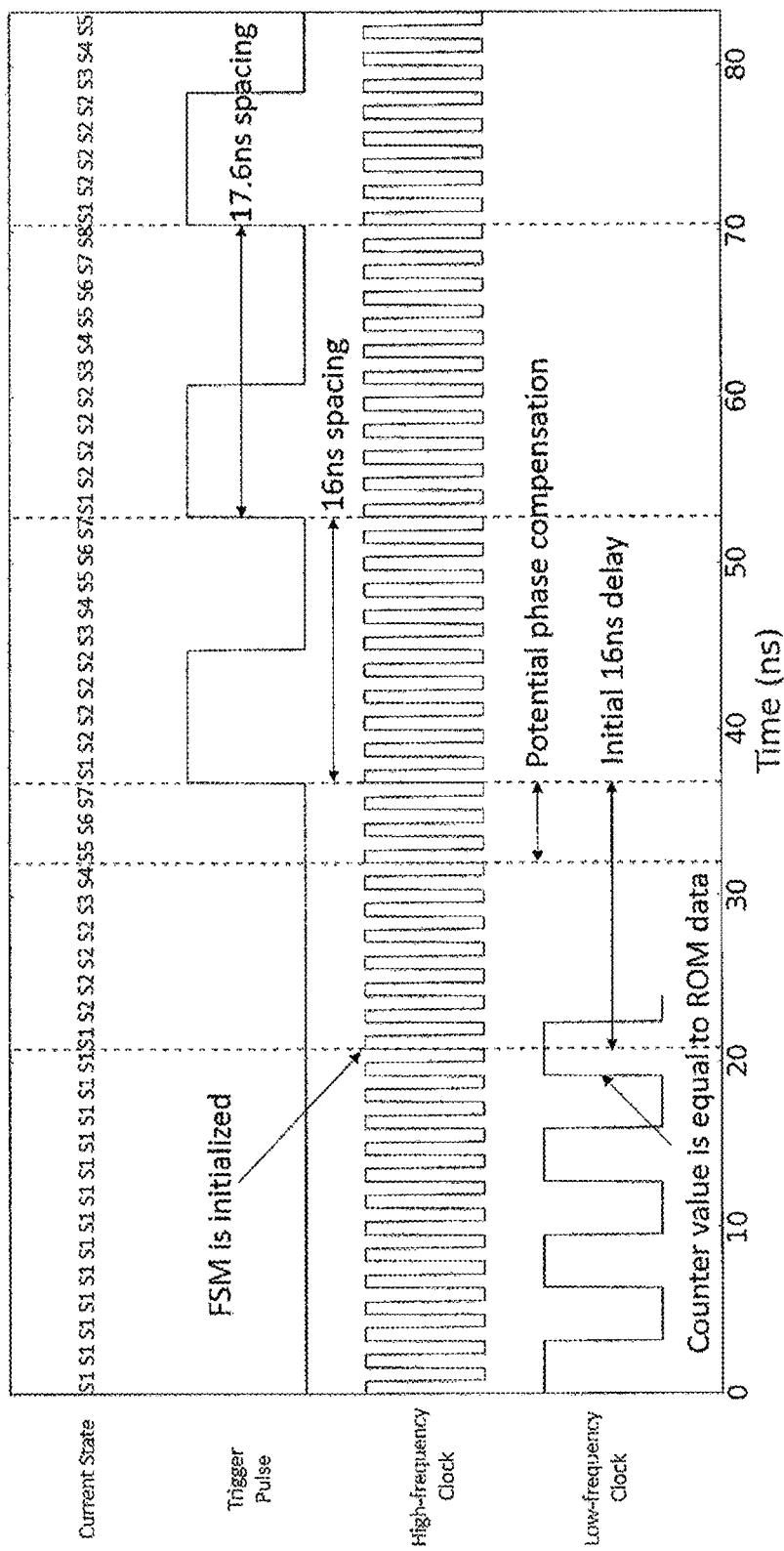
FIG. 17 is a timing diagram illustrating the timing of the output pulse according to one example implementation.

For example, in one example configuration, where the first output sample for a given line/element is 16 ns inside of the high-speed finite state machine with a 1.6 ns dock period, a phase correction be employed to reduce the initial delay provided by the high-speed finite state machine, in order to correct for a timing variation between the low-frequency clock and the high-frequency clock. For example, if the variability of the low-frequency clock is within 6.4 ns, then the high-speed state machine may skip one to three states, in order to reduce the initial delay to 14.4, 12.8, or 11.2 ns. By reducing the time before trigger pulse 535 for the first sample is generated, the timing variability of the low frequency clock can therefore be eliminated (within the quantization error of the high-speed finite state machine). An example implementation of such a timing scheme is shown in FIG. 17, which provides an example timing diagram employing phase compensation to control the timing of the output pulse.

In one example implementation, the high frequency clock may be selected to be 4 times greater than the low frequency clock, however, many other variations may be implemented. Other integer multiples of dock frequencies could be implemented, but the phase compensation inside of the finite state machine would have to be changed accordingly so that the variability of the low frequency clock can be eliminated.

Once the high-speed finite state machine 615 is initialized, it generates successive trigger pulses for the ADC. As per the previously described embodiments, the high-speed finite state machine may be configured such that the delay between successive pulses, within the quantization error of the high-speed finite state machine, corresponds to $n*\frac{1}{4}\lambda$, where n is an odd number (for example, where n=1 and the pulse delay is $a/4\lambda$. It will be understood that the high-speed finite state machine 615 operates at a given clock frequency; thereby each successive sample is quantized to the closest number of clock periods.

As shown in FIG. 11, the high-speed finite state machine receives, for each sample (i.e. on a per-element, per A-line, and per-sample/pixel basis), a fine delay parameter (e.g. fine delay control information) that indicates (and/or may be processed to determine) how many states are executed by the high-speed finite state machine. By controlling the number of states executed in a given cycle, fine delay timing corrections can be applied to each sampling trigger pulse in an efficient method.

In one embodiment, a first subset of states are executed each time the high-speed finite state machine cycle is performed, while the number of states that are executed from a second subset of states are determined based on the fine delay parameter.

In one example implementation, the number of clock periods may be selected, on a per-element, per-A line, and per-pixel basis, using a single bit, where the single bit is employed to determine whether or not a single clock step (state) is included. For example, a single bit may be employed to determine whether or not a given sample is triggered at (N) or (N+1) clock cycles. For the previously described system implementing a 1.6 ns period, the resultant sampling times would be at 16 or 17.6 ns. This feature greatly reduces the requirements of the fine delay ROM as only 1 bit is required to control each sample. Each output sample is used to drive the control unit which manages the addressing of the ROM modules. Then the 1 bit control for the high-speed finite state machine is updated corresponding to the next sample time. In this example implementation, the first subset of states is N states (N clock cycles), and the second subset of states is a single state (corresponding to the N+1th clock cycle). The single bit determines whether or not the single N+1th state is performed.

In another example implementation, two or more bits may be employed to select the states to perform (i.e. number of variable clock cycles to incorporate in the fine delay). For example, two bits may be employed to select one of four states to execute from a subset of four states. Other variations including additional control bits are also possible whereby the system would sample at additional discrete sample spacings.

Further example variations of the aforementioned embodiments include combining any number of the low frequency counters or memory modules for multiple channels. For example, two low frequency counters could be controlled by data stored from one memory module, the resultant outputs could control lour output channels. The preceding method may be preferable over such a method, however, in the interest of reducing high fanout nets and preventing memory collisions.

Figure 12:
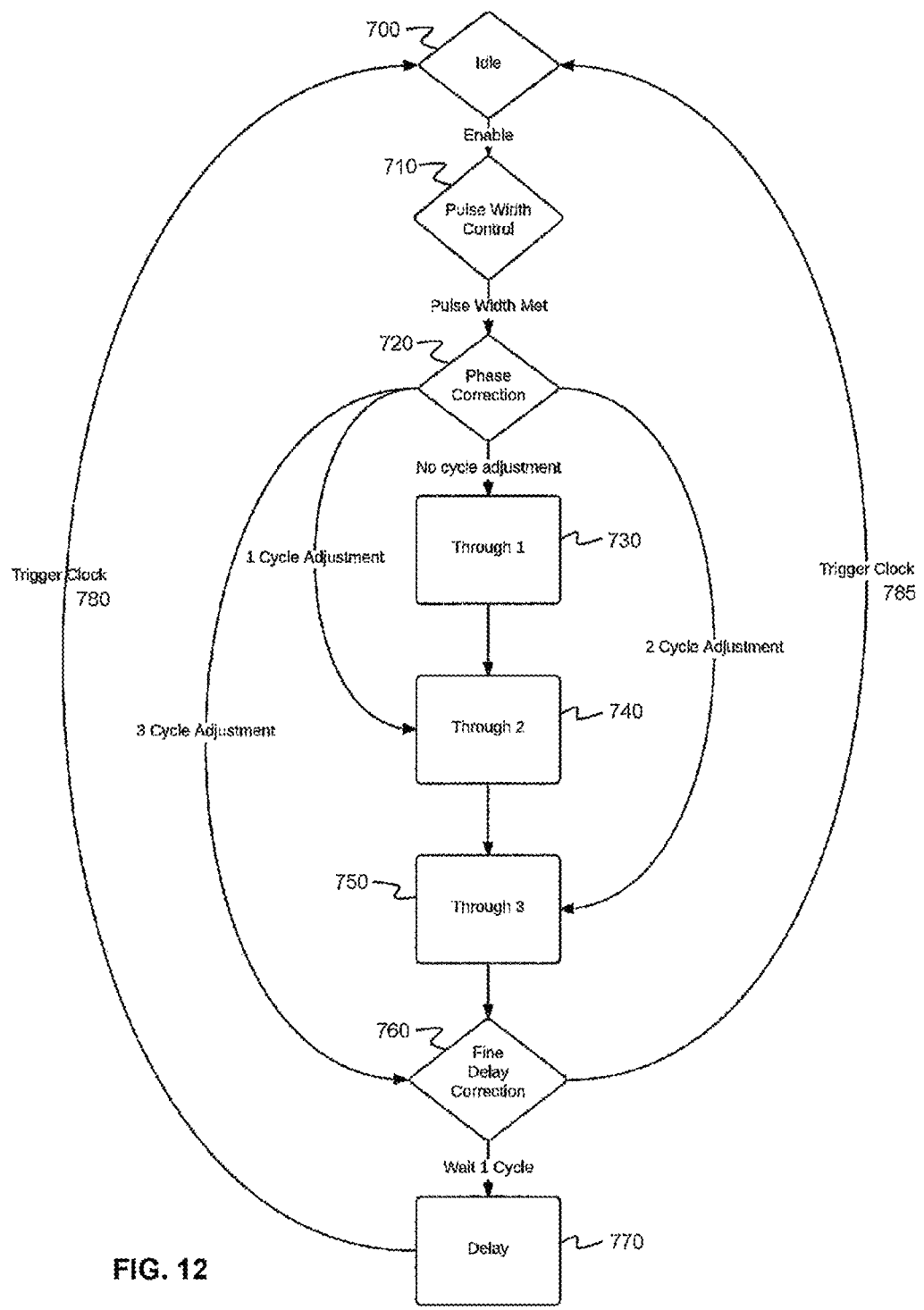
FIG. 12 is an example state diagram that may be implemented by the high-speed finite state machine.

FIG. 12 is a flow chart illustrating an example implementation of the high-speed finite state machine. The high-speed finite state machine remains in an 'idle' state 700 until enabled (e.g. after receiving input from the comparator).

Once enabled, the high-speed finite state machine moves to the first active state 710, which defines the pulse width or duty cycle. This pulse width control block (710) is configured (e.g. hardwired) to count for a predetermined number of clock cycles so that the pulse stays asserted for a total of pre-selected duration (e.g. 8 ns; ~50% duty cycle). This state remains active until a counter reaches a predetermined value corresponding to the pulse width or duty cycle selected. This example feature is introduced to reduce the number of states, in the interest of optimizing for speed but could also be expanded to contain more states or registers. Adding states may result in additional combinational logic which has the potential of introducing problems achieving timing closure in high speed designs. For this reason, reducing the number of states is a preferred method for defining the pulse width or duty cycle. After achieving an appropriate pulse width to meet the application requirements, the state machine checks at state 720 whether or not the phase of the pulse should be adjusted to compensate for the coarse delay, as described above. At this state, the high-speed finite state machine will transition to one of several possible states 730-760 (e.g. one of four states in the preceding example) in order to advance the rising edge of the output pulse accordingly, in order to eliminate timing variability (i.e. reduce the timing variability to a value less than the quantization error of the high-frequency clock) introduced by the low frequency clock. The state to which the high-speed finite state machine is advanced is determined based on the phase compensation value, which may be provided on a per-element, per A-line basis (e.g. by the coarse delay ROM 620 in FIG. 11). Subsequently, the high-speed finite state machine will advance through the remaining states with each clock cycle. This process is represented by "fine delay correction" 760 in FIG. 12, which represents multiple sequential states of the high-speed finite state machine.

Finally, according to the present non-limiting example involving single-bit fine delay correction, the single-bit fine-delay ROM data determines whether the rising edge of the output pulse occurs at the second last or last state (770); corresponding to whether the rising edge occurs at (N) or (N+1) clock cycles. The state machine then generates the trigger pulse (780 or 785) and returns to the idle state and continues to loop until disabled by the control unit.

The present disclosure is also applicable to many applications beyond medical ultrasound imaging. Other example applications that employ echo location using pulses (acoustic, electromagnetic, etc.) and use dynamic receive beamforming include sonic non-destructive testing, underwater array-based sonar, and conventional radar.

EXAMPLES

The following examples are presented to enable those skilled in the art to understand and to practice embodiments of the present disclosure. They should not be considered as a limitation on the scope of the disclosure, but merely as being illustrative and representative thereof.

Example 1—Comparison with Conventional Variable Sampling Method

This example embodiment was demonstrated using a prototype phased array, RF data lines was collected on all channels upsampled to 1.5 GHz using a commercial acquisition card by multiplexing the array elements. The variable sampling method by picking perfect TOF samples out of the large finely sampled data set and adding them together.

Figure 13A:
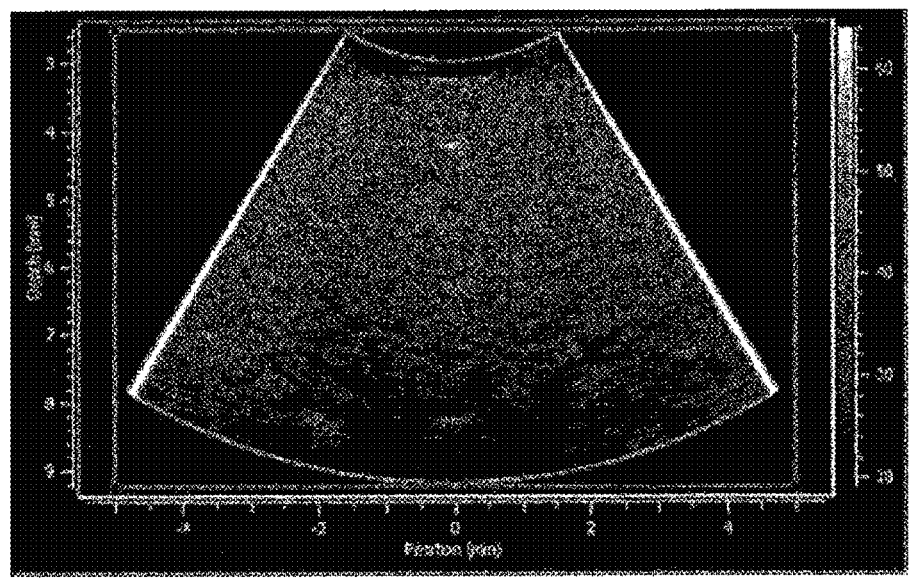
FIGS. 13A and 13B are images showing a comparison of ¼λ vs ¾λ demodulation.
Figure 13B:
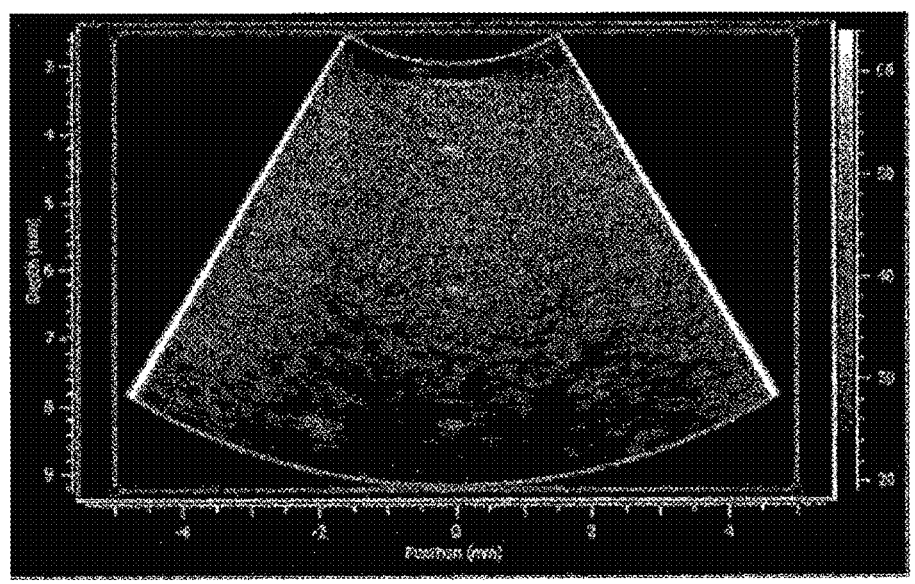

FIGS. 13A and 13B shows comparison images of a tissue phantom between conventional variable sampling and demodulation (with ¼λ, between adjacent I-Q samples), and the example method involving ¾, sampling and demodulation, resulting in no noticeable difference in image quality.

Figure 14:
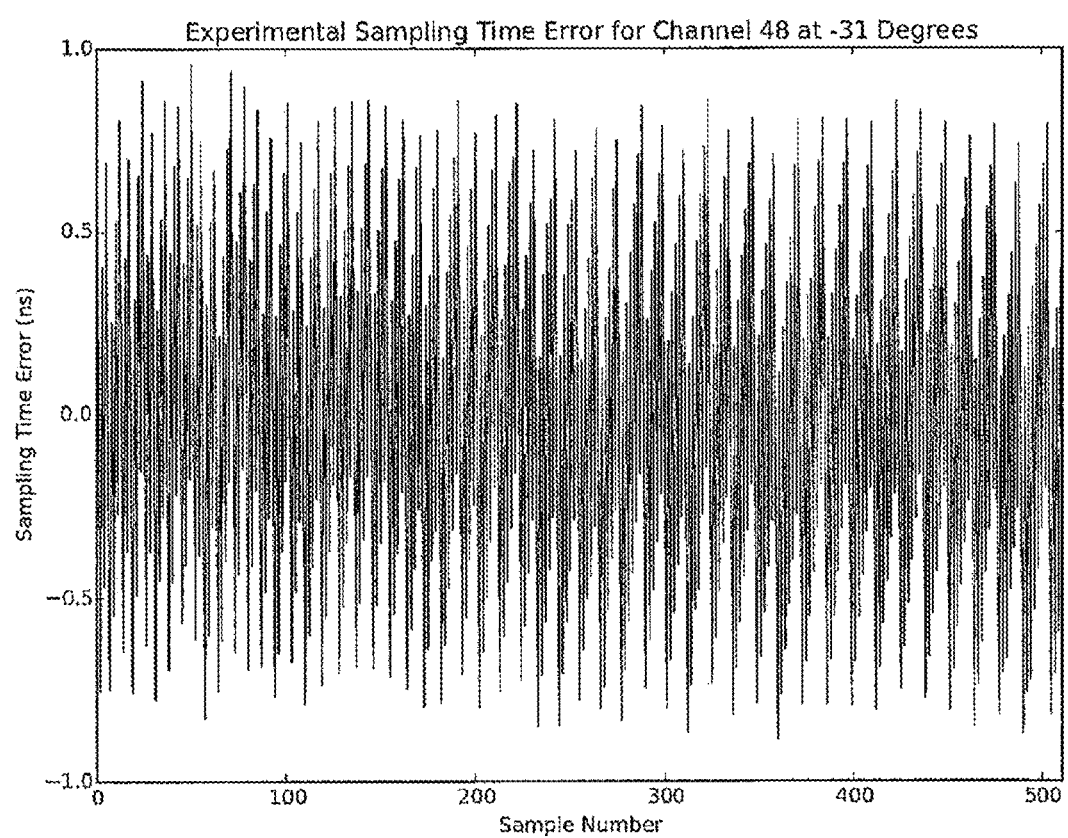
FIG. 14 shows a plot of the measured sampling time error, as a function of sample number, for a single channel of an ultrasound array.
Figure 15:
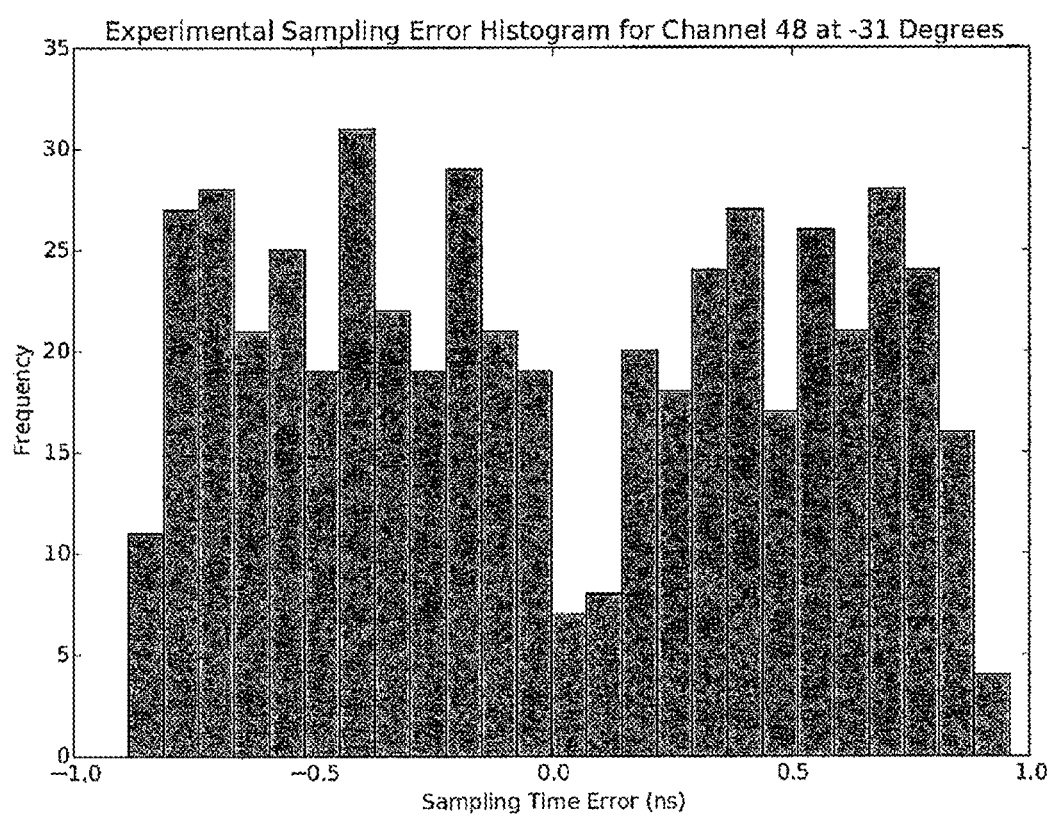
FIG. 15 shows a histogram of the measured sampling time error for a single channel of an ultrasound array, showing that across all samples, the timing error was between −1 and +1 ns.

Example 2—Demonstration of Timing Accuracy Using Receive Beamformer Implemented Using FPGA An example Implementation of the preceding embodiments was developed and tested on an FPGA platform. Preliminary test using 625 MHz high-speed finite state machine and 156.25 MHz low frequency clock on a 64 channel FPGA architecture, with 512 pixels per line, and 64 lines results in sampling accuracy<1 ns. Channel to channel variation was negligible and the sampling error for channel 48 at −31 degrees is shown in FIGS. 14 and 15.

Example 3—Relationship Between Pulse Bandwidth and Amplitude Attenuation Loss

In the present example, a quantitative analysis of the relationship between pulse bandwidth and amplitude attenuation is presented. The bandwidth of the ultrasound pulse is first derived. The ultrasound pulse, defined as p(t), is comprised of both a sine wave and Gaussian component. The respective components have Fourier transforms, S(jw) and R(jw).

$$p(t) = \cos(w_c t) \cdot e^{\frac{-t^2}{2\sigma_w^2}} \quad (1)$$

$$S(jw) = \sqrt{\frac{\pi}{2}} \delta(w - w_c) + \sqrt{\frac{\pi}{2}} \delta(w + w_c) \quad (2)$$

$$R(jw) = \sigma_w \cdot e^{\frac{-w^2 \sigma_w^2}{2}} \quad (3)$$

The Fourier transform P(jw), from p(t), is calculated from the convolution of the Fourier transforms of its respective components S(jw) and R(jw).

$$F[p(t)] = R(jw) * S(jw) \quad (4)$$

$$P(jw) = \sigma_w^2 \sqrt{\frac{\pi}{2}} \cdot (e^{\frac{-(w-w_c)\sigma_w}{2}} + e^{\frac{-(w+w_c)\sigma_w}{2}}) \quad (5)$$

In order to extract the signal bandwidth, the positive frequencies of P(jw) are isolated.

$$P_+(jw) = \sigma_w^2 \sqrt{\frac{\pi}{2}} \cdot e^{\frac{-(w-w_c)\sigma_w}{2}} \quad (6)$$

Bandwidth is defined here as the full width half maximum of the frequency spectrum. Solving for the range of w around $w_c$, to which the Gaussian component of the frequency spectrum is equal to ½, produces the bandwidth in angular frequency. The bandwidth may subsequently be normalized to the center frequency by dividing by $w_c$.

$$\frac{1}{2} = e^{\frac{-(w-w_c)^2 \sigma_w^2}{2}} \quad (7)$$

$$w = w_c \pm \frac{\sqrt{2 \cdot \ln 2}}{\sigma_w} \quad (8)$$

$$BW = w_+ - w_- = 2 \cdot \frac{\sqrt{2 \cdot \ln 2}}{\sigma_w} \quad (9)$$

$$\% \, BW = \frac{2}{w_c \sigma_w} \sqrt{2 \cdot \ln 2} \quad (10)$$

Next, the envelope amplitude decay between successive samples is defined in order to calculate the maximum envelope estimation error. To do so, the Gaussian component of the ultrasound pulse r is rearranged to solve for t. The time between sequential samples Δt is then inferred by taking the difference between two points centered on the pulse peak at a reduced envelope amplitude r.

$$r = e^{\frac{-t^2}{2\sigma_w^2}} \quad (11)$$

$$t = \pm \sigma_w \sqrt{-2 \cdot \ln r} \quad (12)$$

$$\Delta t = t_2 - t_1 = 2\sigma_w \sqrt{-2 \cdot \ln r} \quad (13)$$

The above expression may be manipulated to describe the effective sampling rate. Next the equation is rearranged to express the attenuation r in terms of standard deviation $\sigma_w$ and sampling rate $f_s$.

$$f_s = \frac{1}{\Delta t} = \frac{1}{2\sigma_w\sqrt{-2 \cdot \ln r}} \quad (14)$$

$$r = e^{\frac{-1}{8 \cdot \sigma_w^2 \cdot f_s^2}} \quad (15)$$

For convenience, the expression may then be converted into dB before (13) is rearranged for $\sigma_w$ and substituted into (15).

$$r_{dB} = -20\log\left(e^{\frac{-1}{8 \cdot \sigma_w^2 \cdot f_s^2}}\right) \quad (16)$$

$$r_{dB} = -20\log\left(e^{\frac{-\pi^2}{16 \ln 2}\left(\frac{f_c \cdot \% BW}{f_s}\right)^2}\right) \quad (17)$$

Figure 16:
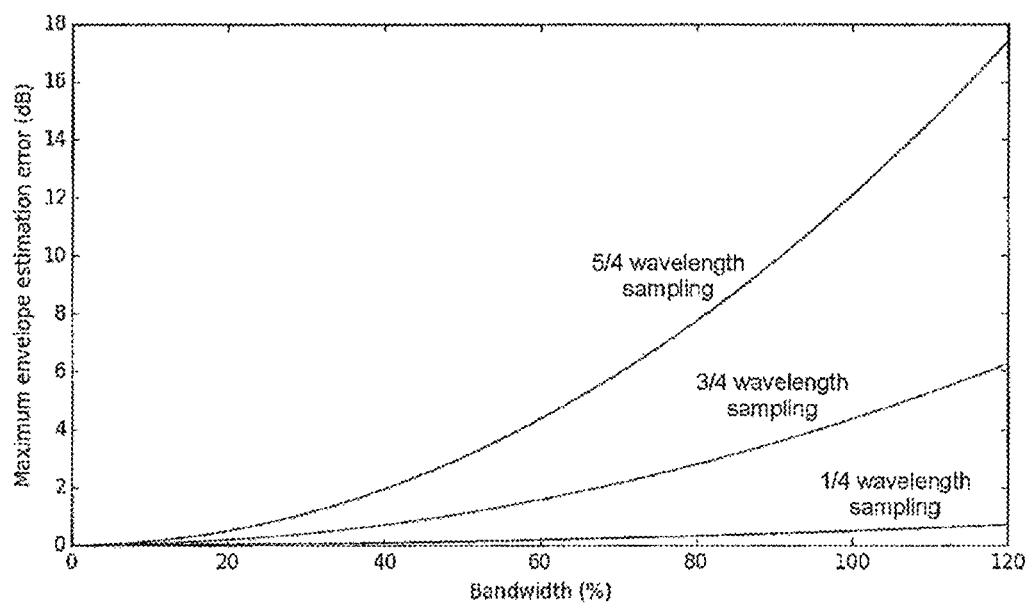
FIG. 16 plots the results from simulations showing envelope amplitude loss as a function of bandwidth and sampling rate.

Using the above equation, the envelope amplitude loss can be plotted across a range of sampling frequencies. FIG. 16 highlights the envelope amplitude loss between samples for ¼, ¾ and 5/4λ sampling as a function of bandwidth. Naturally, as bandwidth increases, the temporal duration of the pulse shortens, and the signal begins to decay before it's sampled.

The curves produced are important for understanding the limitations of sparsely sampling the ultrasound signal for demodulation. For instance, if the envelope must be extracted to within 3 dB, the maximum pulse bandwidth for the ¾ and 5/4 sampling schemes are 83.0 and 49.8% respectively.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

[1] ChangHong Hu, Lequan Zhang, J. M. Cannata and K. K. Shung. Development of a digital high frequency ultrasound array imaging system. Presented at Ultrasonics Symposium (IUS), 2010 IEEE. 2010

[2] B. D. Steinberg "Digital beamforming in ultrasound" IEEE Trans. Ultrason. Ferroelectr. Freq. Control, vol. 39, no. 6, pp. 716-721, 1992

[3] Junying Chen, A. C. H. Yu and H. K.-So. Design considerations of real-time adaptive beamformer for medical ultrasound research using FPGA and GPU. Presented at Feid-Programmable Technology (FPT), 2012 International Conference on. 2012

[4] T. Chemyakoba, Y. C Eldar "Fourier-Domain Beamforming: The Path to Compressed Ultrasound Imaging" IEEE Trans. Ultrason. Ferroelectr. Freq. Control, vol. 61, no 8, 1252-1267, 2014

[5] N. Wagner, Y. C. Eldar and Z. Friedman "Compressed beamforming in ultrasound Imaging" IEEE Trans. Signal Process., vol. 60, no. 9, pp. 46434657, 2012

[6] Y. C. Eldar and G. Kutynlok Compressed Sensing: Theory and Applications. 2012, Cambridge University Press, Cambridge, UK

[7] F. S. Foster, J. D. Larson, R. J. Pittaro, P. D. Corl, A P. Greenstein, and P. K. Lum, "A digital annular array prototype scanner for realtime ultrasound Imaging," Ultrasound Med. Biol., vol. 15, pp. 661-672, 1989.

[8] M. Magrane, "Variable focusing in ultrasound imaging using non-uniform sampling," U.S. Pat. No. 4,669,314 A, Jun. 2, 1987.

[9] J. A. Brown, G. R. Lockwood, "A Digital Beamformer for High-Frequency Annular Arrays," IEEE Trans. on UFFC, Vol. 52, pp. 1262-1269, 2005

[10] A. Bezanson, R. Adamson, M. Bance, J. A. Brown, "Fabrication and Performance of a Miniaturized 64-Element High-Frequency Endoscopic Phased Array," IEEE Trans. on UFFC, Vol 61, pp 33-43, 2014

[11] A. Bezanson, R. Adamson, J. A. Brown, "Fabrication of a Miniaturized 64-Element Phased Array," Proc. IEEE Symp. on Ultrasonics, pp. 2114-2117, 2012

[12] P. Fusaroli, L., G. Caletti, "Forward-view Endoscopic Ultrasound: A Systematic Review of Diagnostic and Therapeutic Applications," Endosc. Ultrasound, Vol. 2, pp. 64-70, 2013

[13] D. Dausch, K. Gilchrist, J. Carlson, S. Hal, J. Castellucci, O. von Ramm, "In vivo real-time 3-D intracardiac echo using PMUT arrays," IEEE Trans. on UFFC, Vol. 61, pp. 1754-1764, 2014

[14] J. A. Brown, Z Torbatian, R. Adamson, R. Van Wijhe, R. J. E. Pennings, G. R. Lockwood, M. L Bance, High-Frequency Ex-Vivo Ultrasound imaging of the Auditory System, Ultrasound in Medicine and Biology, Vol. 35, pp. 1899-1907, 2009

[15] J. Oertel, J. Krauss, M. Gaab, "Ultrasonic aspiration in neuroendoscopy: first results with a new tool," J Neurosurg., Vol 109, pp. 908-911, 2008

[16] J. Stewart, Calculus: Early Transcendentals, Brooks/Cole Publishing Co., Pacific Grove Calif., 1995

[17] J. E. Powers, D. J. Phillips, M. A. Brandestini, R. A. Sigelmann, "Ultrasound Array Delay Lines Based on Quadrature Sampling Techniques," IEEE Trans. On Ultrasonics, Ferroelectrics, & Frequency Control, Vol. SU-27, No. 6, 287-294, 1980

Thereof what is claimed is:

1. A method of performing ultrasound beamforming, the method comprising:
    transmitting a beamformed transmit pulse from an array of ultrasound elements along a selected A-line;
    receiving, with the array of ultrasound elements, received ultrasound signals;
    triggering sampling of the received ultrasound signals, for each ultrasound element, to obtain sampled signals at a plurality of sample times, each sampled signal corresponding to a respective pixel location along the selected A-line, wherein a first sample time along the selected A-line for a given ultrasound element, relative to its respective transmit time, is determined by calculating a round-trip time-of-flight delay between the given ultrasound element and a first pixel location on the selected A-line, and wherein successive samples, corresponding to successive pixel locations along the selected A-line, are obtained such that adjacent samples are spaced by a time interval corresponding to $n\lambda/4$, where n is odd and $\lambda$ is a wavelength of the beamformed transmit pulse, and such that the time interval between adjacent samples is sufficiently small, relative to a pulse envelope of the beamformed transmit pulse, to facilitate demodulation of the ultrasound signals;

for each pixel, combining the sampled signals from the array of ultrasound elements to obtain a beamformed sampled signal; and processing the beamformed sampled signals to generate a waveform associated with the selected A-line, wherein for each pixel, a respective quadrature value is obtained from the beamformed sampled signal associated with an adjacent pixel.

2. The method according to claim 1 wherein combining the sampled signals comprises, for each pixel, adding the sampled signals in absence of the insertion of beamforming delays.

3. The method according to claim 1 wherein the sampled signals from the array of ultrasound elements are processed and combined, in absence of insertion of beamforming delays, to generate the beamformed sampled signal for each pixel.

4. The method according to claim 3 wherein a phase coherence weighting method is employed to process and combine the beamformed sampled signals from the array of ultrasound elements for each pixel.

5. The method according to claim 3 wherein one or more of filtering, apodization, and log compression and Doppler processing is employed to process the sampled signals.

6. The method according to claim 1 wherein the respective pixel locations along the selected A-line are separated such that the time delay between successive samples for each element corresponds to three quarters of a wavelength of the beamformed transmit pulse.

7. The method according to claim 1 further comprising:
generating one or more additional waveforms, each additional waveform corresponding to a respective additional A-line; and
processing the waveforms to generate an image.

8. The method according to claim 1 wherein the sample times, for each ultrasound element, are determined and stored prior to transmitting the beamformed transmit pulse.

9. The method according to claim 1 wherein the triggering of sampling of the received ultrasound signals along the selected A-line, for each ultrasound element, is performed by:

employing a coarse counter, triggered by a low-speed clock, for generating a coarse delay associated with the time-of-flight delay between the ultrasound element and the first pixel along the selected A-line; and repeatedly employing a high-speed finite state machine, comprising a plurality of sequential states that are triggered by a high-speed clock, to generate trigger pulses for triggering acquisition of the samples, the samples corresponding to successive pixel locations along the selected A-line, wherein the trigger pulses are generated such that a delay between adjacent samples equals, within a quantization error associated with the high-speed finite state machine, $n\lambda/4$, where n is odd and $\lambda$ is a wavelength of the beamformed transmit pulse.

10. The method according to claim 9 wherein the high-speed finite state machine is employed, for each element, to generate a phase correction delay associated with the ultrasound element and the selected A-line prior to generating a first trigger pulse, by selecting an initial state from the plurality of sequential states that corrects for a timing error associated with the coarse delay provided by the coarse counter.

11. The method according to claim 9 wherein a fine delay parameter is employed by the high-speed finite state machine to select, for each pixel of a plurality of A-lines, a suitable number of states of the plurality of sequential states to perform in order to control timing of the trigger pulse on a per-element, per-A-line, and per-pixel basis.

12. The method according to claim 11 wherein a first subset of states of the plurality of sequential states are performed each time the high-speed finite state machine is executed, and wherein the fine delay parameter specifies a number of states of a second subset of the plurality of sequential states, to perform in order to control timing of the trigger pulse on a per-element, per-A-line, and per-pixel basis.

13. The method according to claim 12 wherein the second subset of states includes a single state, and wherein the fine delay parameter is a single bit.

14. The method according to claim 11 wherein the fine delay parameter is selected from a fine delay ROM array based on the transducer element, the selected A-line, and the pixel currently being processed.

15. The method according to claim 9 wherein a coarse delay ROM array is employed to specify a coarse delay count for generating the coarse delay for each ultrasound element and for a plurality of A-lines.

16. The method according to claim 15 wherein the coarse delay ROM array is further employed to specify, for each ultrasound element and for a plurality of A-lines, a suitable state of the high-speed finite state machine to correct for the timing error associated with the coarse delay provided by the coarse counter.

17. The method according to claim 1 wherein programmable computer hardware is employed to control the triggering of sampling of the received ultrasound signals.

18. The method according to claim 17 wherein the programmable computer hardware is a field programmable gate array.

19. The method according to claim 1 wherein an application specific integrated circuit is employed to control the triggering of sampling of the received ultrasound signals.

20. An ultrasound beamforming system comprising:
an array of ultrasound elements;
a transmit beamformer operably coupled to said array of ultrasound elements;
a receive beamformer operatively coupled to said array of ultrasound elements;
the receive beamformer comprising computer hardware configured to:
trigger sampling of received ultrasound signals, for each ultrasound element, to obtain sampled signals at a plurality of sample times for a plurality of A-lines, wherein for each ultrasound element and each A-line, each sampled signal corresponding to a respective pixel location along the A-line, and wherein a first sample time along the selected A-line for a given ultrasound element, relative to its respective transmit time, is determined based on a pre-programmed round-trip time-of-flight delay between the given ultrasound element and a first pixel location on the A-line, and wherein successive samples, corresponding to successive pixel locations along the selected A-line, are obtained such that adjacent samples are spaced by a time interval corresponding to $n\lambda/4$, where n is odd and $\lambda$ is a wavelength of the beamformed transmit pulse, and such that the time interval between adjacent samples is sufficiently small, relative to a pulse envelope of the beamformed transmit pulse, to facilitate demodulation of the ultrasound signals;

wherein the receive beamformed is further configured to:
combine, for each A-line, the sampled signals from the array of ultrasound elements to obtain a beamformed sampled signal for each pixel of each A-line; and process the beamformed sampled signals to generate a waveform associated with each A-line, wherein for each pixel, a respective quadrature value is obtained from the beamformed sampled signal associated with an adjacent pixel.

21. The ultrasound imaging system according to claim 20 wherein said computer hardware is programmed to implement, for each ultrasound element:
a coarse counter, triggered by a low-speed clock, for generating a coarse delay associated with the round-trip time-of-flight delay between the ultrasound element and the first pixel along each A-line; and
a high-speed finite state machine, comprising a plurality of sequential states that are triggered by a high-speed clock, to generate trigger pulses for triggering acquisition of the samples, the samples corresponding to successive pixel locations along each A-line, wherein the trigger pulses are generated such that a delay between adjacent samples equals, within a quantization error associated with the high-speed finite state machine, $n\lambda/4$, where n is odd and $\lambda$ is a wavelength of the beamformed transmit pulse.

22. The ultrasound imaging system according to claim 21 wherein the high-speed finite state machine is configured, for each element, to generate a phase correction delay associated with the ultrasound element and the selected A-line prior to generating a first trigger pulse, by selecting an initial state from the plurality of sequential states that corrects for a timing error associated with the coarse delay provided by the coarse counter.

23. The ultrasound imaging system according to claim 21 wherein said computer hardware comprises a fine delay ROM array for providing a fine delay parameter to high-speed finite state machine, such that the high-speed finite state machine is configured to select, for each pixel of a plurality of A-lines, a suitable number of states of the plurality of sequential states to perform in order to control timing of the trigger pulse on a per-element, per-A-line, and per-pixel basis.

24. The ultrasound imaging system according to claim 23 wherein the high-speed finite state machine is configured such that a first subset of states of the plurality of sequential states are performed each time the high-speed finite state machine is executed, and wherein the fine delay parameter specifies a number of states of a second subset of the plurality of sequential states, to perform in order to control timing of the trigger pulse on a per-element, per-A-line, and per-pixel basis.

25. The ultrasound imaging system according to claim 24 wherein the second subset of states includes a single state, and wherein the fine delay parameter is a single bit.

26. The ultrasound imaging system according to claim 21 wherein said computer hardware comprises a coarse delay ROM array that is configured to specify a coarse delay count for generating the coarse delay for each ultrasound element and for the plurality of A-lines.

27. The ultrasound imaging system according to claim 26 wherein the coarse delay ROM array is further employed to specify, for each ultrasound element and for a plurality of A-lines, a suitable state of the high-speed finite state machine to correct for the timing error associated with the coarse delay provided by the coarse counter.

28. The ultrasound imaging system according to claim 21 wherein the said computer hardware is a field programmable gate array.

29. The ultrasound imaging system according to claim 21 wherein said computer hardware is an application specific integrated circuit.

* * * * *